United States Patent
Aissaoui et al.

(10) Patent No.: US 9,096,595 B2
(45) Date of Patent: *Aug. 4, 2015

(54) 7-(HETEROARYL-AMINO)-6,7,8,9-TETRA-HYDROPYRIDO[1,2-A]INDOL ACETIC ACID DERIVATIVES AND THEIR USE AS PROSTAGLANDIN D2 RECEPTOR MODULATORS

(75) Inventors: Hamed Aissaoui, Allschwil (CH); Christoph Boss, Allschwil (CH); Jerome Gabillet, Allschwil (CH); Sylvia Richard-Bildstein, Allschwil (CH); Romain Siegrist, Allschwil (CH)

(73) Assignee: Actelion Pharmaceuticals Ltd, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/111,889

(22) PCT Filed: Apr. 13, 2012

(86) PCT No.: PCT/IB2012/051831
§ 371 (c)(1),
(2), (4) Date: Oct. 15, 2013

(87) PCT Pub. No.: WO2012/140612
PCT Pub. Date: Oct. 18, 2012

(65) Prior Publication Data
US 2014/0045870 A1 Feb. 13, 2014

(30) Foreign Application Priority Data
Apr. 14, 2011 (WO) .................. PCT/IB2011/051615

(51) Int. Cl.
C07D 471/04 (2006.01)
A61K 31/437 (2006.01)
A61P 37/08 (2006.01)

(52) U.S. Cl.
CPC ............ *C07D 471/04* (2013.01); *A61K 31/437* (2013.01)

(58) Field of Classification Search
CPC ........................... C07D 471/04; A61K 31/437
USPC ........................................ 546/94; 514/266.21
See application file for complete search history.

(56) References Cited

U.S. PATENT DOCUMENTS

| 4,808,608 | A | 2/1989 | Guindon et al. |
| 4,965,258 | A | 10/1990 | Boshagen et al. |
| 8,697,869 | B2 * | 4/2014 | Aissaoui et al. ............... 544/294 |
| 2005/0171143 | A1 | 8/2005 | Tanimoto et al. |
| 2007/0191416 | A1 | 8/2007 | Fecher et al. |
| 2007/0208004 | A1 | 9/2007 | Fecher et al. |
| 2009/0270414 | A1 | 10/2009 | Fecher et al. |
| 2010/0063103 | A1 | 3/2010 | Armer et al. |
| 2010/0234396 | A1 | 9/2010 | Fecher et al. |
| 2010/0234415 | A1 * | 9/2010 | Berthelette et al. ........... 514/294 |
| 2011/0311483 | A1 | 12/2011 | Jia et al. |

FOREIGN PATENT DOCUMENTS

| EP | 0 242 518 B1 | 4/1991 |
| EP | 1 505 061 | 2/2005 |
| EP | 1 600 440 | 11/2005 |
| EP | 1 852 420 | 11/2007 |
| EP | 1 911 759 | 4/2008 |
| EP | 1 916 245 | 4/2008 |
| EP | 1 932 839 | 6/2008 |
| GB | 2 388 540 | 11/2003 |
| GB | 2 407 318 | 4/2005 |
| GB | 2 422 829 | 8/2006 |
| GB | 2 422 830 | 8/2006 |
| GB | 2 422 831 | 8/2006 |
| WO | WO 01/78697 | 10/2001 |
| WO | WO 01/79169 | 10/2001 |
| WO | WO 02/094830 | 11/2002 |
| WO | WO 03/051837 | 6/2003 |
| WO | WO 03/062200 | 7/2003 |
| WO | WO 03/066046 | 8/2003 |
| WO | WO 03/066047 | 8/2003 |
| WO | WO 03/097042 | 11/2003 |

(Continued)

OTHER PUBLICATIONS

Arimura A. et al., "Prevention of Allergic Inflammation by a Novel Prostaglandin Receptor Antagonist, S-5751," J. Pharmacol. Exp. Ther. (2001), vol. 298, No. 2, pp. 411-419.

(Continued)

*Primary Examiner* — John Mabry
*Assistant Examiner* — Daniel Carcanague
(74) *Attorney, Agent, or Firm* — Hunton & Williams LLP

(57) ABSTRACT

The present invention relates to 7-(heteroaryl-amino)-6,7,8, 9-tetrahydropyrido[1,2-a]indol acetic acid derivatives of the formula (I),

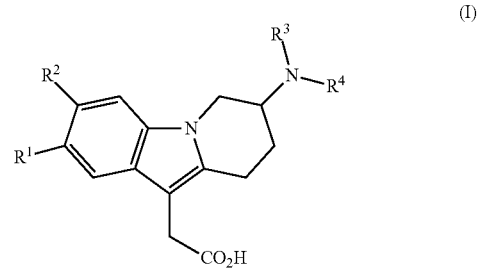

wherein $R^1$, $R^2$, $R^3$ and $R^4$ are as described in the description and their use as prostaglandin receptor modulators, most particularly as prostaglandin $D_2$ receptor modulators, in the treatment of various prostaglandin-mediated diseases and disorders, to pharmaceutical compositions containing these compounds and to processes for their preparation.

18 Claims, No Drawings

(56) References Cited

FOREIGN PATENT DOCUMENTS

| | | |
|---|---|---|
| WO | WO 03/101961 | 12/2003 |
| WO | WO 03/101981 | 12/2003 |
| WO | WO 2004/007451 | 1/2004 |
| WO | WO 2004/039807 | 5/2004 |
| WO | WO 2004/103970 | 12/2004 |
| WO | WO 2004/106302 | 12/2004 |
| WO | WO 2004/111047 | 12/2004 |
| WO | WO 2005/019171 | 3/2005 |
| WO | WO 2005/033099 | 4/2005 |
| WO | WO 2005/040112 | 5/2005 |
| WO | WO 2005/040114 | 5/2005 |
| WO | WO 2005/044260 | 5/2005 |
| WO | WO 2005/054232 | 6/2005 |
| WO | WO 2005/056527 | 6/2005 |
| WO | WO 2005/073234 | 8/2005 |
| WO | WO 2005/121141 | 12/2005 |
| WO | WO 2005/123731 | 12/2005 |
| WO | WO 2006/034418 | 3/2006 |
| WO | WO 2006/034419 | 3/2006 |
| WO | WO 2006/036994 | 4/2006 |
| WO | WO 2006/063763 | 6/2006 |
| WO | WO 2006/081343 | 8/2006 |
| WO | WO 2006/092579 | 9/2006 |
| WO | WO 2006/095183 | 9/2006 |
| WO | WO 2006/125784 | 11/2006 |
| WO | WO 2006/136859 | 12/2006 |
| WO | WO 2007/019675 | 2/2007 |
| WO | WO 2007/022501 | 2/2007 |
| WO | WO 2007/031747 | 3/2007 |
| WO | WO 2007/045867 | 4/2007 |
| WO | WO 2007/065683 | 6/2007 |
| WO | WO 2007/065684 | 6/2007 |
| WO | WO 2007/065924 | 6/2007 |
| WO | WO 2007/068418 | 6/2007 |
| WO | WO 2007/107772 | 9/2007 |
| WO | WO 2007/138282 | 12/2007 |
| WO | WO 2007/144127 | 12/2007 |
| WO | WO 2008/012511 | 1/2008 |
| WO | WO 2008/014186 | 1/2008 |
| WO | WO 2008/017989 | 2/2008 |
| WO | WO 2008/074966 | 6/2008 |
| WO | WO 2008/078069 | 7/2008 |
| WO | WO 2008/113965 | 9/2008 |
| WO | WO 2009/044134 | 4/2009 |
| WO | WO 2009/044147 | 4/2009 |
| WO | WO 2009/049021 | 4/2009 |
| WO | WO 2009/061676 | 5/2009 |
| WO | WO 2009/063202 | 5/2009 |
| WO | WO 2009/063215 | 5/2009 |
| WO | WO 2009/077728 | 6/2009 |
| WO | WO 2009/090399 | 7/2009 |
| WO | WO 2009/090414 | 7/2009 |
| WO | WO 2009/093026 | 7/2009 |
| WO | WO 2009/093029 | 7/2009 |
| WO | WO 2009/096526 | 8/2009 |
| WO | WO 2009/140642 | 11/2009 |
| WO | WO 2010/006939 | 1/2010 |
| WO | WO 2010/006944 | 1/2010 |
| WO | WO 2010/008864 | 1/2010 |
| WO | WO 2010/031182 | 3/2010 |
| WO | WO 2010/031183 | 3/2010 |
| WO | WO 2010/031184 | 3/2010 |
| WO | WO 2010/039982 | 4/2010 |
| WO | WO 2010/054113 | 5/2010 |
| WO | WO 2010/054114 | 5/2010 |
| WO | WO 2010/085820 | 7/2010 |
| WO | WO 2010/099039 | 9/2010 |
| WO | WO 2010/142934 | 12/2010 |
| WO | WO 2011/006936 | 1/2011 |
| WO | WO 2011/055270 | 5/2011 |
| WO | WO 2011/117798 | 9/2011 |
| WO | WO 2012/009134 | 1/2012 |
| WO | WO 2012/009137 | 1/2012 |

OTHER PUBLICATIONS

Birkinshaw T. N.et al., "Discovery of potent CRTh2 ($DP_2$) receptor antagonists," Bioorg. Med. Chem Let. (2006) vol. 16, pp. 4287-4290.

Gallant M. et al., "Discovery of MK-7246, a selective CRTH2 antagonist for the treatment of respiratory diseases," Bioorg. Med. Chem Let. (2011), vol. 21, pp. 288-293.

Gould, Philip, "Salt selection for basic drugs," International Journal of Pharmaceuticals (1986), vol. 33, pp. 201-217.

Grimster N. et al., "Palladium-Catalyzed Intermolecular Alkenylation of Indoles by Solvent-Controlled Regioselective C—H Functionalization," Angewandte Chemie (2005), vol. 44, pp. 3125-3129.

Ha J.D. et. al., "Synthesis of Tetrahydrocarbazole Derivatives as Potent β3-Andrenoceptor Agonists," Bulletin of the Korean Chemical Society, (2004), vol. 25 No. 12, pp. 1784-1790.

Ishizuka, T. et al., "Ramatroban (BAY u3405): A Novel Dual Antagonist of $TXA_2$ Receptor and CRTh2, A Newly Identified Prostaglandin $D_2$ Receptor" Cardiovascular Drug Rev. (2004), vol. 22, No. 2, pp. 71-90.

Luker Tim et al., "Substituted indole-1-acetic acids as potent and selective CRTH2 antagonist—discovery of AZD1981," Bioorg. Med. Chem Let. (2011) vol. 21, pp. 6288-6292.

Remington: "The Science and Practice of Pharmacy," $21^{st}$ Edition, Lippincott, Williams and Wilkins Publishing, The University of the Sciences in Philadelphia, 2005.

Robarge M. J. et al., "Isosteric Ramatroban Analogs: Selective and Potent CRTH-2 Antagonists," Bioorg. Med. Chem Let. (2005) vol. 15, pp. 1749-1753.

Rosentreter U et al., "Synthesis and Absolute Configuration of the New Thromboxane Antagonist (3R)-3-(4-Fluorophenylsulfonamido)-1,2,3,4-tetrahydro-9-carbazolepropanoic Acid and Comparison with its Enantiomer," (1989) Arzneimittelforschung, vol. 39, No. 12, pp. 1519-1521.

Royer, J. F et al., "A novel antagonist of prostaglandin D2 blocks the locomotion of eosinophils and basophils," Europ. J. Clin. Investigation (2008), vol. 38, pp. 663-671.

Sandham, David A. et al., "7-Azaindole-3-acetic Acid Derivatives: Potent and Selective CRTh2 Receptor Antagonist" Bioorg. Med. Chem Let. (2009), vol. 19, pp. 4794-4798.

Sawyer, N. et al., "Molecular Pharmacology of the Human Prostaglandin $D_2$ Receptor, CRTH2" Br. J. Pharmacology (2002), vol. 137, pp. 1163-1172.

Stearns Brian A. et al., "Novel tricyclic antagonists of the prostaglandin D2 receptor DP2 with efficacy in a murine model of allergic rhinitis" Bioorg. Med. Chem Let. (2009), vol. 19, pp. 4647-4651.

Sugimoto H. et al., "An Orally Bioavalable Small Molecule Antagonist of CRTH2, Ramatroban (BAY u3405), Inhibits Prostaglandin $D_2$-Induced Eosinophil Migration in Vitro," J. Pharmacol. Exp. Ther. (2003), vol. 305, No. 1, pp. 347-352.

Tumey, L. Nathan et al., "3-Indolyl sultams as selective CRTh2 antagonists," Bioorg. Med. Chem Let. (2010), vol. 20, pp. 3287-3290.

Ulven T. et al., "Synthesis and in vitro evaluation of a selective antagonist and the corresponding radioligand for the prostaglandin $D_2$ receptor CRTH2," Bioorg. Med. Chem Let. (2007) vol. 17, pp. 5924-5927.

Ulven T. et al., "Minor Structural Modifications Convert the Dual TP/CRTH2 Antagonist Ramatroban into a Highly Selective and Potent CRTH2 Antagonist," J. Med. Chem. (2005), vol. 48, No. 4, pp. 897-900.

International Search Report of PCT/IB2012/051831, mailed Jun. 25, 2012.

* cited by examiner

7-(HETEROARYL-AMINO)-6,7,8,9-TETRAHYDROPYRIDO[1,2-A]INDOL ACETIC ACID DERIVATIVES AND THEIR USE AS PROSTAGLANDIN D2 RECEPTOR MODULATORS

CROSS-REFERENCE TO RELATED APPLICATIONS

This application is the U.S. National Phase of International Patent Application No. PCT/IB2012/051831, filed Apr. 13, 2012, which claims priority to PCT/IB2011/051615, filed Apr. 14, 2011, the contents of each are hereby incorporated by reference in their entireties.

FIELD OF THE INVENTION

The present invention relates to 7-(heteroaryl-amino)-6,7,8,9-tetrahydropyrido[1,2-a]indol acetic acid derivatives of formula (I) and their use as prostaglandin receptor modulators, most particularly as prostaglandin $D_2$ receptor ("DP receptor") modulators, in the treatment of various prostaglandin-mediated diseases and disorders, to pharmaceutical compositions containing these compounds and to processes for their preparation. In particular, such derivatives may be used alone or in pharmaceutical compositions for the treatment of both, chronic and acute allergic/immune diseases/disorders such as asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease and rheumatoid arthritis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinohilic endocarditis (Loeffler's endocarditis), eosinophilia-myalgia syndrome, eosinophilic fasciitis, eosinohilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms); and basophil-related diseases, comprising basophilic leukemia and basophilic leukocytosis.

BACKGROUND OF THE INVENTION

As a response to allergen exposure in allergic conditions, mast cells are activated and release mediators like histamine, thromboxane A2 (TxA2), cysteinyl leukotrienes (CysLTs) and prostaglandin $D_2$ ($PGD_2$). These mediators interact with their respective receptors and cause physiological effects such as increased vascular permeability, edema, pruritus, nasal and pulmonary congestion, bronchoconstriction, and mucus secretion. An increased vascular permeability for example, allows excessive infiltration of eosinophilic and basophilic leukocytes into the tissue and thus amplifies the allergic response.

Current treatments of allergic diseases comprise agents that can block or otherwise interrupt such interactions, e.g. anti-histamines (histamine H1 receptor antagonists), leukotriene receptor antagonists, beta-adrenergic receptor agonists, and corticosteroids. Generally, treatments with anti-histamines and leukotriene antagonists are limited in efficacy, and long-term usage of corticosteroids is often associated with unwanted side effects.

$PGD_2$ is an agonist known to act on two G-protein-coupled receptors, the $PGD_2$ receptor DP1 and the recently identified CRTH2 (chemoattractant receptor-homologous molecule expressed on Th2 cells) receptor (also referred to as "DP2 receptor").

Elevated $PGD_2$ levels are considered to cause inflammation as observed in allergic diseases such as allergic rhinitis, allergic asthma, allergic conjunctivitis, atopic dermatitis and the like. Therefore, blocking the interaction of $PGD_2$ with its receptors is considered a useful therapeutic strategy for the treatment of such diseases.

GB 2388540 discloses the use of ramatroban ((3R)-3-(4-fluorobenzene-sulfonamido)-1,2,3,4-tetrahydrocarbazole-9-propionic acid), a TxA2 receptor (also referred to as "TP receptor") antagonist with additional antagonistic activity on CRTH2, for the prophylaxis and treatment of allergic diseases, such as asthma, allergic rhinitis or allergic conjunctivitis. In T. Ishizuka et al., Cardiovascular Drug Rev. 2004, 22(2), 71-90 effects of ramatroban on late-phase inflammation are described. Furthermore, oral bioavailability of ramatroban and its ability to inhibit prostaglandin $D_2$-induced eosinophil migration in vitro has been reported (Journal of Pharmacology and Experimental Therapeutics, 305(1), p. 347-352 (2003)).

WO 2003/097598 and WO 2003/097042 disclose Ramatroban analogues with CRTH2 antagonistic activity. Ulven et al, J. Med. Chem. 2005, 48(4), 897-900 disclose further ramatroban analogues.

WO 2008/017989 discloses (3-amino-1,2,3,4-tetrahydro-9H-carbazol-9-yl)-acetic acid derivatives with CRTH2 antagonistic activity. WO 2011/117798 discloses 3-(heteroaryl-amino)-1,2,3,4-tetrahydro-9H-carbazole derivatives.

WO 2007/019675, WO 2010/031182 and WO 2010/031183 disclose different 6,7,8,9-tetrahydro-pyrido[1,2-a]indol acetic acid derivatives with CRTH2 antagonistic activity. WO 10/031,184 discloses azaindole derivatives with CRTH2 antagonistic activity.

DESCRIPTION OF THE INVENTION

1) The present invention relates to 7-(heteroaryl-amino)-6,7,8,9-tetrahydropyrido[1,2-a]indol acetic acid derivatives of the formula (I),

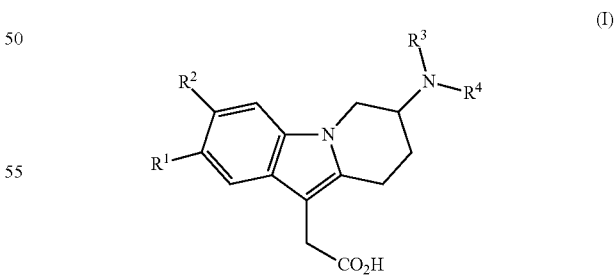

wherein
$R^1$ and $R^2$ represent independently of each other hydrogen, $(C_1-C_4)$alkyl, $(C_1-C_4)$alkoxy, halogen, trifluoromethoxy or trifluoromethyl;
$R^3$ represents hydrogen, $(C_1-C_4)$alkyl, $(C_1-C_2)$alkoxy-$(C_2-C_3)$alkyl, $(C_1-C_4)$fluoroalkyl or $(C_3-C_6)$cycloalkyl-$(C_1-C_2)$alkyl; and $R^4$ represents a heteroaryl group which is unsubstituted or mono-, di- or tri-substituted, wherein the substituents are independently selected from the group consisting of halogen, $(C_1-C_4)$alkyl, $(C_3-C_6)$cycloalkyl, $(C_1-C_4)$alkoxy, $(C_1-C_4)$fluoroalkyl and phenyl (preferably from halogen, $(C_1-C_4)$alkyl and $(C_1-C_4)$fluoroalkyl);

and to the salts (in particular pharmaceutically acceptable salts) of such compounds.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

The following paragraphs provide definitions of the various chemical moieties for the compounds according to the invention and are intended to apply uniformly throughout the specification and claims unless an otherwise expressly set out definition provides a broader or narrower definition.

The term "alkyl", used alone or in combination, refers to a straight or branched chain alkyl group containing one to four carbon atoms. The term "$(C_x-C_y)$alkyl" (x and y each being an integer), refers to an alkyl group as defined before containing x to y carbon atoms. For example a $(C_1-C_4)$alkyl group contains from one to four carbon atoms. Representative examples of alkyl groups include methyl, ethyl, n-propyl, iso-propyl, n-butyl, iso-butyl, sec-butyl and tert-butyl.

In case "$R^1$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec-butyl and tert-butyl. Preferred is methyl.

In case "$R^2$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec-butyl and tert-butyl. Preferred is methyl.

In case "$R^3$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec-butyl and tert-butyl. Preferred are methyl, ethyl, n-propyl, iso-propyl and iso-butyl; more preferred are methyl, ethyl and n-propyl; most preferred is methyl.

In case "$R^4$" represents "heteroaryl which is substituted with $(C_1-C_4)$alkyl" the term "$(C_1-C_4)$alkyl" means $(C_1-C_4)$alkyl groups as defined above. Examples of said groups are methyl, ethyl, n-propyl, iso-propyl, n-butyl, iso-butyl, sec-butyl and tert-butyl. Preferred is methyl.

The term "alkoxy", used alone or in combination, refers to an alkyl-O— group wherein the alkyl group is as defined before. The term "$(C_x-C_y)$alkoxy" (x and y each being an integer) refers to an alkoxy group as defined before containing x to y carbon atoms. For example a $(C_1-C_4)$alkoxy group contains from one to four carbon atoms. Representative examples of alkoxy groups include methoxy, ethoxy, n-propoxy, iso-propoxy, n-butoxy, iso-butoxy, sec-butoxy and tert-butoxy.

In case "$R^1$" represents "$(C_1-C_4)$alkoxy" the term means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$R^2$" represents "$(C_1-C_4)$alkoxy" the term means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$R^4$" represents "heteroaryl which is substituted with $(C_1-C_4)$alkoxy" the term "$(C_1-C_4)$alkoxy" means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

The term "$(C_1-C_2)$alkoxy-$(C_2-C_3)$alkyl" refers to an $(C_2-C_3)$alkyl group as defined above in which one hydrogen atom has been replaced with an $(C_1-C_2)$alkoxy group as defined above. Examples of $(C_1-C_2)$alkoxy-$(C_2-C_3)$alkyl groups are methoxy-ethyl (notably 2-methoxy-ethyl), methoxy-propyl (notably 2-methoxy-propyl and 3-methoxy-propyl), ethoxy-ethyl (notably 2-ethoxy-ethyl) and ethoxy-propyl (notably 2-ethoxy-propyl and 3-ethoxy-propyl). Preferred is 2-methoxy-ethyl.

The term "$(C_3-C_6)$cycloalkyl", used alone or in combination, means a cycloalkyl group with 3 to 6 carbon atoms. Examples of $(C_3-C_6)$cycloalkyl groups are cyclopropyl, cyclobutyl, cyclopentyl and cyclohexyl. Preferred is cyclopropyl.

The term "$(C_3-C_6)$cycloalkyl-$(C_1-C_2)$-alkyl" refers to an $(C_1-C_2)$alkyl group as defined above in which one hydrogen atom has been replaced with an $(C_3-C_6)$cycloalkyl group as defined above. Examples of $(C_3-C_6)$cycloalkyl-$(C_1-C_2)$alkyl groups are cyclopropyl-methyl, cyclobutyl-methyl, cyclopentyl-methyl, cyclohexyl-methyl, cyclopropyl-ethyl (notably 1-cyclopropyl-ethyl and 2-cyclopropyl-ethyl), cyclobutyl-ethyl (notably 1-cyclobutyl-ethyl and 2-cyclobutyl-ethyl), cyclopentyl-ethyl (notably 1-cyclopentyl-ethyl and 2-cyclopentyl-ethyl) and cyclohexyl-ethyl (notably 1-cyclohexyl-ethyl and 2-cyclohexyl-ethyl). Preferred is cyclopropyl-methyl.

The term "$(C_x-C_y)$fluoroalkyl" (x and y each being an integer) refers to an alkyl group as defined before containing x to y carbon atoms in which one or more (and possibly all) hydrogen atoms have been replaced with fluorine. For example a $(C_1-C_4)$fluoroalkyl group contains from one to four carbon atoms in which one to nine hydrogen atoms have been replaced with fluorine.

In case "$R^3$" represents "$(C_1-C_4)$fluoroalkyl" the term means a $(C_1-C_4)$fluoroalkyl group as defined above. Examples of said groups are difluoromethyl, trifluoromethyl, 2,2-difluoroethyl and 2,2,2-trifluoroethyl. Preferred examples are 2,2-difluoroethyl and 2,2,2-trifluoroethyl. Most preferred is 2,2-difluoroethyl.

In case "$R^4$" represents "heteroaryl which is substituted with $(C_1-C_4)$fluoroalkyl" the term "$(C_1-C_4)$fluoroalkyl" means a $(C_1-C_4)$fluoroalkyl group as defined above. Examples of said groups are difluoromethyl, trifluoromethyl, 2,2-difluoroethyl and 2,2,2-trifluoroethyl. Preferred examples are difluoromethyl and trifluoromethyl. Most preferred is trifluoromethyl.

The term halogen means fluoro, chloro, bromo or iodo.

In case "$R^1$" represents "halogen" the term means preferably fluorine and chlorine and most preferably fluorine.

In case "$R^2$" represents "halogen" the term means preferably fluorine and chlorine and most preferably fluorine.

In case "$R^4$" represents "heteroaryl which is substituted with halogen" the term "halogen" means preferably fluorine, chlorine and bromine, more preferably fluorine and chlorine and most preferably chlorine.

The term "heteroaryl", used alone or in combination, means a 5- to 10-membered monocyclic or bicyclic aromatic ring containing 1, 2 or 3 heteroatoms independently selected from oxygen, nitrogen and sulfur. Preferably the term "heteroaryl" means a 5- to 10-membered monocyclic or bicyclic aromatic ring containing one nitrogen atom and optionally one additional heteroatom selected from oxygen, nitrogen and sulfur. Most preferred are 6-membered monocyclic aromatic ring systems containing one or two nitrogen atoms. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, cinnolinyl, quinazolinyl, quinoxalinyl and phthalazinyl. Preferred examples of such heteroaryl groups are pyridyl (notably pyridin-2-yl), pyrimidyl (notably pyrimidin-2-yl), benzoxazolyl (notably benzoxazol-2-yl), benzothiazolyl (notably benzothiazol-2-yl) and quinazolinyl (notably quinazolin-2-yl and quinazolin-4-yl). Further preferred examples are isoxazolyl (notably isoxazol-3-yl), thiazolyl (notably thiazol-2-yl), thiadiazolyl (notably thiadiazol-2-yl), pyrazolyl (notably pyrazol-3-yl) and quinoxalinyl (notably quinoxalin-2-yl). More preferred are pyrimidyl (notably pyrimidin-2-yl), benzoxazolyl (notably benzoxazol-2-yl) and benzothiazolyl (notably benzothiazol-2-yl). Most preferred is pyrimidyl (notably pyrimidin-2-yl). The heteroaryl group may be unsubstituted or mono-, di- or tri-substituted (preferably unsubstituted or mono-substituted and most preferably mono-substituted), wherein the substituents are independently selected from the group consisting of halogen, $(C_1$-$C_4)$alkyl, $(C_3$-$C_6)$cycloalkyl, $(C_1$-$C_4)$alkoxy, $(C_1$-$C_4)$fluoroalkyl and phenyl. Examples of such unsubstituted, mono-, di- or tri-substituted heteroaryl groups are 5-fluoro-pyrimidin-2-yl, 5-chloro-pyrimidin-2-yl, 5-trifluoromethyl-pyrimidin-2-yl, 5-fluoro-benzoxazol-2-yl, 6-fluoro-benzoxazol-2-yl, 5-fluoro-benzothiazol-2-yl, and 6-fluoro-benzothiazol-2-yl. Further examples are 5-methyl-pyrimidin-2-yl, quinazolin-2-yl, 6-fluoro-quinazolin-2-yl, 7-fluoro-quinazolin-2-yl, 2-methyl-quinazolin-4-yl and 6-fluoro-quinoxalin-2-yl. Preferred examples are 5-fluoro-pyrimidin-2-yl, 5-chloro-pyrimidin-2-yl, 5-methyl-pyrimidin-2-yl, 5-fluoro-benzoxazol-2-yl, 6-fluoro-benzoxazol-2-yl, quinazolin-2-yl, 7-fluoro-quinazolin-2-yl and 6-fluoro-quinoxalin-2-yl. More preferred examples are 5-fluoro-pyrimidin-2-yl, 5-chloro-pyrimidin-2-yl, 5-fluoro-benzoxazol-2-yl, and 6-fluoro-benzoxazol-2-yl. Most preferred are 5-fluoro-pyrimidin-2-yl and 5-chloro-pyrimidin-2-yl.

2) A further embodiment of the invention relates to compounds according to embodiment 1), wherein
$R^1$ represents hydrogen, $(C_1$-$C_4)$alkyl, $(C_1$-$C_4)$alkoxy, halogen or trifluoromethoxy;
$R^2$ represents hydrogen, halogen or trifluoromethyl;
$R^3$ represents hydrogen, $(C_1$-$C_4)$alkyl, $(C_1$-$C_2)$alkoxy-$(C_2$-$C_3)$alkyl, $(C_1$-$C_4)$fluoroalkyl or $(C_3$-$C_6)$cycloalkyl-$(C_1$-$C_2)$alkyl; and
$R^4$ represents a heteroaryl group which is unsubstituted or mono- or di-substituted, wherein the substituents are independently selected from the group consisting of halogen, $(C_1$-$C_4)$alkyl, $(C_3$-$C_6)$cycloalkyl, $(C_1$-$C_4)$alkoxy, $(C_1$-$C_4)$fluoroalkyl and phenyl (preferably from halogen, $(C_1$-$C_4)$alkyl and $(C_1$-$C_4)$fluoroalkyl);
and to the salts (in particular pharmaceutically acceptable salts) of such compounds.

3) A further embodiment of the invention relates to compounds according to embodiment 1), wherein
$R^1$ represents hydrogen, $(C_1$-$C_4)$alkyl, $(C_1$-$C_4)$alkoxy, halogen or trifluoromethoxy;
$R^2$ represents hydrogen, halogen or trifluoromethyl;
$R^3$ represents hydrogen or $(C_1$-$C_4)$alkyl; and
$R^4$ represents a heteroaryl group which is unsubstituted or mono- or di-substituted (notably mono-substituted), wherein the substituents are independently selected from the group consisting of halogen, $(C_1$-$C_4)$alkyl and $(C_1$-$C_4)$fluoroalkyl (preferably from halogen and $(C_1$-$C_4)$fluoroalkyl);
and to the salts (in particular pharmaceutically acceptable salts) of such compounds.

4) A further embodiment of the invention relates to compounds according to embodiment 1), wherein
$R^1$ represents hydrogen, methyl, methoxy, fluoro, chloro or trifluoromethoxy (notably hydrogen);
$R^2$ represents hydrogen, fluoro, chloro or trifluoromethyl (notably fluoro, chloro or trifluoromethyl);
$R^3$ represents hydrogen or methyl; and
$R^4$ represents a heteroaryl group which is unsubstituted or mono-substituted with fluoro, chloro or trifluoromethyl (notably fluoro or chloro);
and to the salts (in particular pharmaceutically acceptable salts) of such compounds.

5) A further embodiment of the invention relates to compounds according to embodiment 1), wherein
$R^1$ represents hydrogen;
$R^2$ represents hydrogen, fluoro, chloro or trifluoromethyl (notably fluoro or chloro);
$R^3$ represents methyl; and
$R^4$ represents a heteroaryl group which is mono-substituted with fluoro or chloro, wherein the heteroaryl group is selected from pyrimidin-2-yl, benzoxazol-2-yl and benzothiazol-2-yl;
and to the salts (in particular pharmaceutically acceptable salts) of such compounds.

6) A further embodiment of the invention relates to compounds according to any one of embodiments 1) to 4), wherein
$R^1$ represents hydrogen, $(C_1$-$C_4)$alkyl or halogen (notably hydrogen, methyl, fluoro or chloro);
and to the salts (in particular pharmaceutically acceptable salts) of such compounds.

7) A further embodiment of the invention relates to compounds according to any one of embodiments 1) to 4), wherein
$R^1$ represents hydrogen or halogen (notably hydrogen, fluoro or chloro); and to the salts (in particular pharmaceutically acceptable salts) of such compounds.

8) A further embodiment of the invention relates to compounds according to any one of embodiments 1) to 5), wherein
$R^1$ represents hydrogen;
and to the salts (in particular pharmaceutically acceptable salts) of such compounds.

9) A further embodiment of the invention relates to compounds according to any one of embodiments 1) to 3) or 6) to 8), wherein
$R^2$ represents hydrogen, halogen or trifluoromethyl;
and to the salts (in particular pharmaceutically acceptable salts) of such compounds.

10) A further embodiment of the invention relates to compounds according to any one of embodiments 1) to 4) or 6) to 8), wherein
$R^2$ represents hydrogen, fluoro, chloro or trifluoromethyl;
and to the salts (in particular pharmaceutically acceptable salts) of such compounds.

11) A further embodiment of the invention relates to compounds according to any one of embodiments 1) to 8), wherein
$R^2$ represents fluoro or chloro;
and to the salts (in particular pharmaceutically acceptable salts) of such compounds.

12) A further embodiment of the invention relates to compounds according to any one of embodiments 1), 2) or 6) to 11), wherein
$R^3$ represents hydrogen, $(C_1-C_4)$alkyl, $(C_1-C_2)$alkoxy-$(C_2-C_3)$alkyl or $(C_3-C_6)$cycloalkyl-$(C_1-C_2)$alkyl;
and to the salts (in particular pharmaceutically acceptable salts) of such compounds.

13) A further embodiment of the invention relates to compounds according to any one of embodiments 1), 2) or 6) to 11), wherein
$R^3$ represents hydrogen, methyl, ethyl, n-propyl, 2-methoxyethyl, 2,2-difluoroethyl or cyclopropyl-methyl;
and to the salts (in particular pharmaceutically acceptable salts) of such compounds.

14) A further embodiment of the invention relates to compounds according to any one of embodiments 1) to 4) or 6) to 11), wherein
$R^3$ represents hydrogen or methyl;
and to the salts (in particular pharmaceutically acceptable salts) of such compounds.

15) A further embodiment of the invention relates to compounds according to any one of embodiments 1) to 11), wherein
$R^3$ represents $(C_1-C_4)$alkyl (notably methyl);
and to the salts (in particular pharmaceutically acceptable salts) of such compounds.

16) A further embodiment of the invention relates to compounds according to any one of embodiments 1) to 4) or 6) to 11), wherein
$R^3$ represents hydrogen;
and to the salts (in particular pharmaceutically acceptable salts) of such compounds.

17) A further embodiment of the invention relates to compounds according to any one of embodiments 1), 2) or 6) to 16), wherein
$R^4$ represents a heteroaryl group which is unsubstituted or mono- or di-substituted (notably mono-substituted), wherein the substituents are independently selected from the group consisting of halogen, $(C_1-C_4)$alkyl, $(C_3-C_6)$cycloalkyl, $(C_1-C_4)$alkoxy and $(C_1-C_4)$fluoroalkyl;
and to the salts (in particular pharmaceutically acceptable salts) of such compounds.

18) A further embodiment of the invention relates to compounds according to any one of embodiments 1), 2) or 6) to 16), wherein
$R^4$ represents a heteroaryl group which is unsubstituted or mono-substituted (notably mono-substituted) with halogen, $(C_3-C_6)$cycloalkyl or $(C_1-C_4)$fluoroalkyl (notably fluorine, chlorine, cyclopropyl or trifluoromethyl);
and to the salts (in particular pharmaceutically acceptable salts) of such compounds.

19) A further embodiment of the invention relates to compounds according to any one of embodiments 1) to 3) or 6) to 16), wherein
$R^4$ represents a heteroaryl group which is mono-substituted with halogen or $(C_1-C_4)$fluoroalkyl (notably fluoro, chloro or trifluoromethyl);
and to the salts (in particular pharmaceutically acceptable salts) of such compounds.

20) A further embodiment of the invention relates to compounds according to any one of embodiments 1) to 16), wherein
$R^4$ represents a heteroaryl group which is mono-substituted with fluoro or chloro;
and to the salts (in particular pharmaceutically acceptable salts) of such compounds.

21) A further embodiment of the invention relates to compounds according to any one of embodiments 17) to 20), wherein
the heteroaryl group is selected from pyrimidyl (notably pyrimidin-2-yl), benzoxazolyl (notably benzoxazol-2-yl) and benzothiazolyl (notably benzothiazol-2-yl);
and to the salts (in particular pharmaceutically acceptable salts) of such compounds.

22) A further embodiment of the invention relates to compounds according to any one of embodiments 17) to 20), wherein
the heteroaryl group is pyrimidyl (notably pyrimidin-2-yl);
and to the salts (in particular pharmaceutically acceptable salts) of such compounds.

23) A further embodiment of the invention relates to compounds according to any one of embodiments 17) to 20), wherein
the heteroaryl group is benzoxazolyl (notably benzoxazol-2-yl);
and to the salts (in particular pharmaceutically acceptable salts) of such compounds.

24) A further embodiment of the invention relates to compounds according to any one of embodiments 17) to 20), wherein
the heteroaryl group is benzothiazolyl (notably benzothiazol-2-yl);
and to the salts (in particular pharmaceutically acceptable salts) of such compounds.

25) A further embodiment of the invention relates to compounds according to any one of embodiments 1) to 24), wherein the absolute configuration of the stereogenic center is as depicted in formula $I_{St1}$

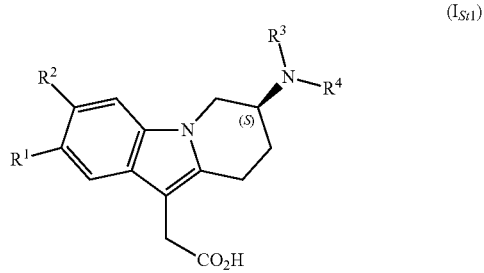

$(I_{St1})$ and to the salts (in particular pharmaceutically acceptable salts) of such compounds.

26) A further embodiment of the invention relates to compounds according to any one of embodiments 1) to 24), wherein the absolute configuration of the stereogenic center is as depicted in formula $I_{St2}$

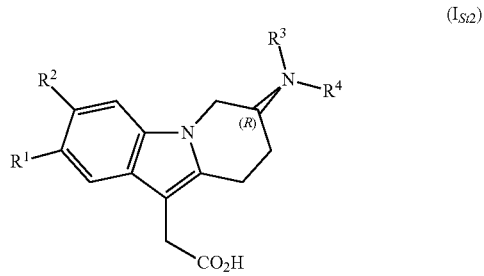

$(I_{St2})$ and to the salts (in particular pharmaceutically acceptable salts) of such compounds.

27) Preferred compounds of formula (I) as defined in embodiment 1) are selected from the group consisting of:
- 2-(7-((5-chloropyrimidin-2-yl)(methyl)amino)-6,7,8,9-tetrahydropyrido[1,2-a]indol-10-yl)acetic acid;
- 2-(7-((5-fluoropyrimidin-2-yl)(methyl)amino)-6,7,8,9-tetrahydropyrido[1,2-a]indol-10-yl)acetic acid;
- 2-(7-(methyl(5-(trifluoromethyl)pyrimidin-2-yl)amino)-6,7,8,9-tetrahydropyrido[1,2-a]indol-10-yl)acetic acid;
- 2-(7-((6-fluorobenzo[d]thiazol-2-yl)(methyl)amino)-6,7,8,9-tetrahydropyrido[1,2-a]indol-10-yl)acetic acid;
- 2-(7-((5-fluorobenzo[d]oxazol-2-yl)(methyl)amino)-6,7,8,9-tetrahydropyrido[1,2-a]indol-10-yl)acetic acid;
- 2-(7-((5-fluorobenzo[d]thiazol-2-yl)(methyl)amino)-6,7,8,9-tetrahydropyrido[1,2-a]indol-10-yl)acetic acid;
- 2-(2-fluoro-7-((5-fluoropyrimidin-2-yl)(methyl)amino)-6,7,8,9-tetrahydropyrido[1,2-a]indol-10-yl)acetic acid,
- 2-(2-fluoro-7-((5-fluorobenzo[d]oxazol-2-yl)(methyl)amino)-6,7,8,9-tetrahydropyrido[1,2-a]indol-10-yl)acetic acid;
- 2-(3-fluoro-7-((5-fluoropyrimidin-2-yl)(methyl)amino)-6,7,8,9-tetrahydropyrido[1,2-a]indol-10-yl)acetic acid;
- 2-(3-fluoro-7-((5-fluorobenzo[d]oxazol-2-yl)(methyl)amino)-6,7,8,9-tetrahydropyrido[1,2-a]indol-10-yl)acetic acid;
- 2-(7-((5-fluoropyrimidin-2-yl)(methyl)amino)-2-methoxy-6,7,8,9-tetrahydropyrido[1,2-a]indol-10-yl)acetic acid;
- 2-(7-((5-fluorobenzo[d]oxazol-2-yl)(methyl)amino)-2-methoxy-6,7,8,9-tetrahydropyrido[1,2-a]indol-10-yl)acetic acid;
- 2-(7-((5-fluoropyrimidin-2-yl)(methyl)amino)-2-methyl-6,7,8,9-tetrahydropyrido[1,2-a]indol-10-yl)acetic acid;
- 2-(7-((5-fluorobenzo[d]oxazol-2-yl)(methyl)amino)-2-methyl-6,7,8,9-tetrahydropyrido[1,2-a]indol-10-yl)acetic acid;
- 2-(2-chloro-7-((5-fluoropyrimidin-2-yl)(methyl)amino)-6,7,8,9-tetrahydropyrido[1,2-a]indol-10-yl)acetic acid;
- 2-(2-chloro-7-((5-fluorobenzo[d]oxazol-2-yl)(methyl)amino)-6,7,8,9-tetrahydropyrido[1,2-a]indol-10-yl)acetic acid;
- 2-(7-((5-chloropyrimidin-2-yl)(methyl)amino)-3-fluoro-6,7,8,9-tetrahydropyrido[1,2-a]indol-10-yl)acetic acid;
- 2-(3-fluoro-7-(methyl(5-(trifluoromethyl)pyrimidin-2-yl)amino)-6,7,8,9-tetrahydropyrido[1,2-a]indol-10-yl)acetic acid;
- 2-(3-fluoro-7-((5-fluorobenzo[d]thiazol-2-yl)(methyl)amino)-6,7,8,9-tetrahydropyrido[1,2-a]indol-10-yl)acetic acid;
- 2-(3-fluoro-7-((6-fluorobenzo[d]oxazol-2-yl)(methyl)amino)-6,7,8,9-tetrahydropyrido[1,2-a]indol-10-yl)acetic acid;
- 2-(3-chloro-7-((5-chloropyrimidin-2-yl)(methyl)amino)-6,7,8,9-tetrahydropyrido[1,2-a]indol-10-yl)acetic acid;
- 2-(7-((5-chloropyrimidin-2-yl)(methyl)amino)-3-(trifluoromethyl)-6,7,8,9-tetrahydropyrido[1,2-a]indol-10-yl)acetic acid;
- 2-(7-((5-chloropyrimidin-2-yl)(methyl)amino)-2-(trifluoromethoxy)-6,7,8,9-tetrahydropyrido[1,2-a]indol-10-yl)acetic acid;
- 2-(7-((5-fluoropyrimidin-2-yl)(methyl)amino)-3-(trifluoromethyl)-6,7,8,9-tetrahydropyrido[1,2-a]indol-10-yl)acetic acid;
- 2-(7-((5-fluoropyrimidin-2-yl)(methyl)amino)-2-(trifluoromethoxy)-6,7,8,9-tetrahydropyrido[1,2-a]indol-10-yl)acetic acid;
- 2-(7-((6-fluorobenzo[d]thiazol-2-yl)(methyl)amino)-3-(trifluoromethyl)-6,7,8,9-tetrahydropyrido[1,2-a]indol-10-yl)acetic acid;
- 2-(7-((6-fluorobenzo[d]thiazol-2-yl)(methyl)amino)-2-(trifluoromethoxy)-6,7,8,9-tetrahydropyrido[1,2-a]indol-10-yl)acetic acid;
- 2-(7-((5-fluorobenzo[d]oxazol-2-yl)(methyl)amino)-3-(trifluoromethyl)-6,7,8,9-tetrahydropyrido[1,2-a]indol-10-yl)acetic acid;
- 2-(7-((5-fluorobenzo[d]oxazol-2-yl)(methyl)amino)-2-(trifluoromethoxy)-6,7,8,9-tetrahydropyrido[1,2-a]indol-10-yl)acetic acid;
- 2-(3-chloro-7-((5-fluoropyrimidin-2-yl)(methyl)amino)-6,7,8,9-tetrahydropyrido[1,2-a]indol-10-yl)acetic acid;
- 2-(3-chloro-7-((5-fluorobenzo[d]oxazol-2-yl)(methyl)amino)-6,7,8,9-tetrahydropyrido[1,2-a]indol-10-yl)acetic acid;
- (S)-2-(3-chloro-7-((5-fluoropyrimidin-2-yl)(methyl)amino)-6,7,8,9-tetrahydropyrido[1,2-a]indol-10-yl)acetic acid;
- (R)-2-(3-chloro-7-((5-fluoropyrimidin-2-yl)(methyl)amino)-6,7,8,9-tetrahydropyrido[1,2-a]indol-10-yl)acetic acid;
- 2-(3-fluoro-7-((5-fluoropyrimidin-2-yl)amino)-6,7,8,9-tetrahydropyrido[1,2-a]indol-10-yl)acetic acid;
- 2-(3-fluoro-7-((5-fluorobenzo[d]oxazol-2-yl)amino)-6,7,8,9-tetrahydropyrido[1,2-a]indol-10-yl)acetic acid;
- 2-(3-chloro-7-((5-fluoropyrimidin-2-yl)amino)-6,7,8,9-tetrahydropyrido[1,2-a]indol-10-yl)acetic acid; and
- 2-(3-chloro-7-((5-chloropyrimidin-2-yl)amino)-6,7,8,9-tetrahydropyrido[1,2-a]indol-10-yl)acetic acid;

or salts (in particular pharmaceutically acceptable salts) of such compounds;

it is to be understood for any of the above listed compounds, that a stereogenic center, which is not specifically assigned, may be in absolute (R)- or absolute (S)-configuration.

28) Further preferred compounds of formula (I) as defined in embodiment 1) are selected from the group consisting of:
- 2-(3-chloro-7-(methyl(5-methylpyrimidin-2-yl)amino)-6,7,8,9-tetrahydropyrido[1,2-a]indol-10-yl)acetic acid;
- 2-(3-chloro-7-(methyl(quinazolin-2-yl)amino)-6,7,8,9-tetrahydropyrido[1,2-a]indol-10-yl)acetic acid;
- 2-(3-chloro-7-((6-fluoroquinazolin-2-yl)(methyl)amino)-6,7,8,9-tetrahydropyrido[1,2-a]indol-10-yl)acetic acid;
- 2-(3-chloro-7-((7-fluoroquinazolin-2-yl)(methyl)amino)-6,7,8,9-tetrahydropyrido[1,2-a]indol-10-yl)acetic acid;
- 2-(3-chloro-7-(methyl(2-methylquinazolin-4-yl)amino)-6,7,8,9-tetrahydropyrido[1,2-a]indol-10-yl)acetic acid;
- 2-(3-chloro-7-((6-fluoroquinoxaline-2-yl)(methyl)amino)-6,7,8,9-tetrahydropyrido[1,2-a]indol-10-yl)acetic acid;
- 2-(3-chloro-7-((2,2-difluoroethyl)(5-fluorobenzo[d]oxazol-2-yl)amino)-6,7,8,9-tetrahydropyrido[1,2-a]indol-10-yl)acetic acid;
- 2-(3-chloro-7-(ethyl(5-fluoropyrimidin-2-yl)amino)-6,7,8,9-tetrahydropyrido[1,2-a]indol-10-yl)acetic acid;
- 2-(3-chloro-7-((5-fluorobenzo[d]oxazol-2-yl)(isopropyl)amino)-6,7,8,9-tetrahydropyrido[1,2-a]indol-10-yl)acetic acid;
- 2-(3-chloro-7-((5-fluoropyrimidin-2-yl)(2-methoxyethyl)amino)-6,7,8,9-tetrahydropyrido[1,2-a]indol-10-yl)acetic acid;
- 2-(3-chloro-7-((5-fluorobenzo[d]oxazol-2-yl)(isobutyl)amino)-6,7,8,9-tetrahydropyrido[1,2-a]indol-10-yl)acetic acid;
- 2-(3-chloro-7-((5-fluoropyrimidin-2-yl)(propyl)amino)-6,7,8,9-tetrahydropyrido[1,2-a]indol-10-yl)acetic acid;
- 2-(3-chloro-7-(ethyl(5-fluorobenzo[d]oxazol-2-yl)amino)-6,7,8,9-tetrahydropyrido[1,2-a]indol-10-yl)acetic acid; and 2-(3-chloro-7-((cyclopropylmethyl)(5-fluoropyrimidin-2-yl)amino)-6,7,8,9-tetrahydropyrido[1,2-a]indol-10-yl)acetic acid;

or salts (in particular pharmaceutically acceptable salts) of such compounds;

it is to be understood for any of the above listed compounds, that a stereogenic center, which is not specifically assigned, may be in absolute (R)- or absolute (S)-configuration.

Unless explicitly stated otherwise, the general terms and names used hereinbefore and hereinafter preferably have within the context of this disclosure the following meanings:

Where the plural form is used for compounds, salts, pharmaceutical compositions, diseases and the like, this is intended to mean also a single compound, salt, or the like.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The compounds of formula (I) according to any one of embodiments 1) to 28), or pharmaceutically acceptable salts thereof, may be used for the preparation of a medicament, and are suitable for the prevention and/or treatment of diseases selected from the group consisting of chronic and acute allergic/immune diseases/disorders, comprising asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease and rheumatoid arthritis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms); and basophil-related diseases, comprising basophilic leukemia and basophilic leukocytosis.

In a preferred embodiment, the compounds of formula (I) according to any one of embodiments 1) to 28), or pharmaceutically acceptable salts thereof, may be used for the preparation of a medicament, and are suitable for the prevention and/or treatment of diseases selected from the group consisting of asthma, allergic asthma, eosinophilic asthma, severe asthma, allergic rhinitis, angioedema, insect venom allergy, drug allergies, allergic sinusitis, allergic nephritis, allergic conjunctivitis, atopic dermatitis, food allergy, systemic mast cell disorders, anaphylactic shock, urticaria and eczema.

In another preferred embodiment, the compounds of formula (I) according to any one of embodiments 1) to 28), or pharmaceutically acceptable salts thereof, may be used for the preparation of a medicament, and are suitable for the prevention and/or treatment of diseases selected from the group consisting of eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms).

In yet another preferred embodiment, the compounds of formula (I) according to any one of embodiments 1) to 28), or pharmaceutically acceptable salts thereof, may be used for the preparation of a medicament, and are suitable for the prevention and/or treatment of diseases selected from the group consisting of basophil-related diseases, comprising basophilic leukemia and basophilic leukocytosis.

The invention also relates to the use of a compound of formula (I) according to any one of embodiments 1) to 28) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 28).

A pharmaceutical composition according to the present invention contains at least one compound of formula (I) according to any one of embodiments 1) to 28) (or a pharmaceutically acceptable salt thereof) as the active agent and optionally carriers and/or diluents and/or adjuvants.

The compounds of formula (I) according to any one of embodiments 1) to 28) and their pharmaceutically acceptable salts can be used as medicaments, e.g. in the form of pharmaceutical compositions for enteral (such as especially oral) or parenteral (including topical application or inhalation) administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 28), or a pharmaceutically acceptable salt thereof.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

Any reference to a compound of formula (I), (I$_{ST1}$) or (I$_{ST2}$) in this text is to be understood as referring also to the salts (and especially the pharmaceutically acceptable salts) of such compounds, as appropriate and expedient. The preferences indicated for the compounds of formula (I) of course apply mutatis mutandis to the compounds of formula (I$_{ST1}$) and the compounds of formula (I$_{ST2}$) as well as to the salts and pharmaceutically acceptable salts of the compounds of formula (I), of formula (I$_{ST1}$) or of formula (I$_{ST2}$). The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range or if a variable is defined as being an integer between 1 and 4, this means that the variable is the integer 1, 2, 3, or 4.

As mentioned earlier, compounds of formula (I) modulate the PGD$_2$ activation of the CRTH2 receptor. The biological effect of such compounds may be tested in a variety of in vitro, ex vivo and in vivo assays. The ability of the compounds of formula (I) to bind to the CRTH2 receptor may be measured by methods similar to those described in the literature (Arimura A. et al., *J. Pharmacol. Exp. Ther.* 2001, 298(2), 411-419; and Sawyer N. et al., *Br. J. Pharmacol*, 2002, 137, 1163-1172, respectively) and by the assays described below in the experimental part.

A further aspect of the invention is a process for the preparation of compounds of formula (I). Compounds according to formula (I) of the present invention can be prepared according to the sequence of reactions outlined in the schemes below wherein R$^1$, R$^2$, R$^3$ and R$^4$ are as defined for formula (I). Other abbreviations used are defined in the experimental section. In some instances the generic groups R$^1$, R$^2$, R$^3$ and R$^4$ might be incompatible with the assembly illustrated in the schemes below and, therefore, will require the use of protecting groups (PG). For example it may be necessary to protect reactive functional groups such as hydroxy, amino, imino, thio or carboxy groups, where these are desired in the final product, to avoid their unwanted participation in the reactions. The use of protecting groups is well known in the art. It will be assumed that such protecting groups are as necessary in place.

In general, all chemical transformations can be performed according to well-known standard methodologies as described in the literature, or as described in the procedures below. The compounds obtained may also be converted into pharmaceutically acceptable salts thereof in a manner known per se.

The compounds of formula (I) may be prepared from the respective (E)-ethyl 3-(1-(2-(tert-butoxy)-2-oxoethyl)-1H-indol-2-yl)acrylate derivatives (4). Compounds (4) are obtained by reaction of the corresponding (E)-ethyl 3-(1H-indol-2-yl)acrylate derivatives (3) with tert-butyl bromoacetate in the presence of a base such as Cs$_2$CO$_3$ in an aprotic solvent such as DMF. The (E)-ethyl 3-(1H-indol-2-yl)acrylate derivatives (3) may be prepared either via Wittig reaction from commercially available or well-known 1H-indole-2-carbaldehyde derivatives (1) by reaction with carbethoxymethylene triphenylphosphorane in an aprotic solvent such as DCM or via Heck reaction from commercially available or well known indole derivatives (2) by reaction with ethyl acrylate in the presence of a catalyst such as Pd(OAc)$_2$ and an oxidant such as tert-butyl perbenzoate in a mixture of AcOH and dioxane (Gaunt M. J. et al, Angewandte Chemie, 2005, 44, 3125-3129).

Hydrogenation of the obtained (E)-ethyl 3-(1-(2-(tert-butoxy)-2-oxoethyl)-1H-indol-2-yl)acrylate derivatives (4) over a catalyst such as Pd—C 10% or PtO$_2$ in an aprotic solvent such as EA followed by reaction with KOtBu in an aprotic solvent such as THF gives the corresponding tert-butyl 7-oxo-6,7,8,9-tetrahydropyrido[1,2-a]indole-6-carboxylate derivatives (5). Decarboxylation by reaction with silica gel in an aprotic solvent such as toluene and subsequent reductive aminations with, first, benzylamine in the presence of a reducing agent such NaBH(OAc)$_3$ in an aprotic solvent such as DCM, and with, second, an appropriate aldehyde (as precursor of R$^3$) in the presence of a reducing agent such NaBH$_4$ in a protic solvent such as MeOH gives the corresponding N-benzyl-6,7,8,9-tetrahydropyrido[1,2-a]indol-7-amine derivatives (6). Friedel-Craft acylation with oxalyl chloride in an aprotic solvent such as DCM, followed by esterification with MeOH and subsequent reduction with triethylsilane in the presence of TFA gives the corresponding methyl 2-(7-(benzylamino)-6,7,8,9-tetrahydropyrido[1,2-a]indol-10-yl)acetate derivatives (7). Debenzylation by hydrogenation over a catalyst such as Pd—C 10% in a protic solvent such as EtOH or by reaction with 1-chloroethyl chloroformate and MeOH in an aprotic solvent such as DCM gives the respective N-substituted methyl 2-(7-amino-6,7,8,9-tetrahydropyrido[1,2-a]indol-10-yl)acetate derivatives (8). Reaction with an appropriate heteroaryl halide like R$^4$—Cl in the presence of a base such as K$_2$CO$_3$ in an aprotic solvent such as DMA followed by saponification with a base such as NaOH furnished the compounds of formula (I) (Method A).

Scheme 1: General synthetic route for the preparation of compounds of formula (I)
(Method A)
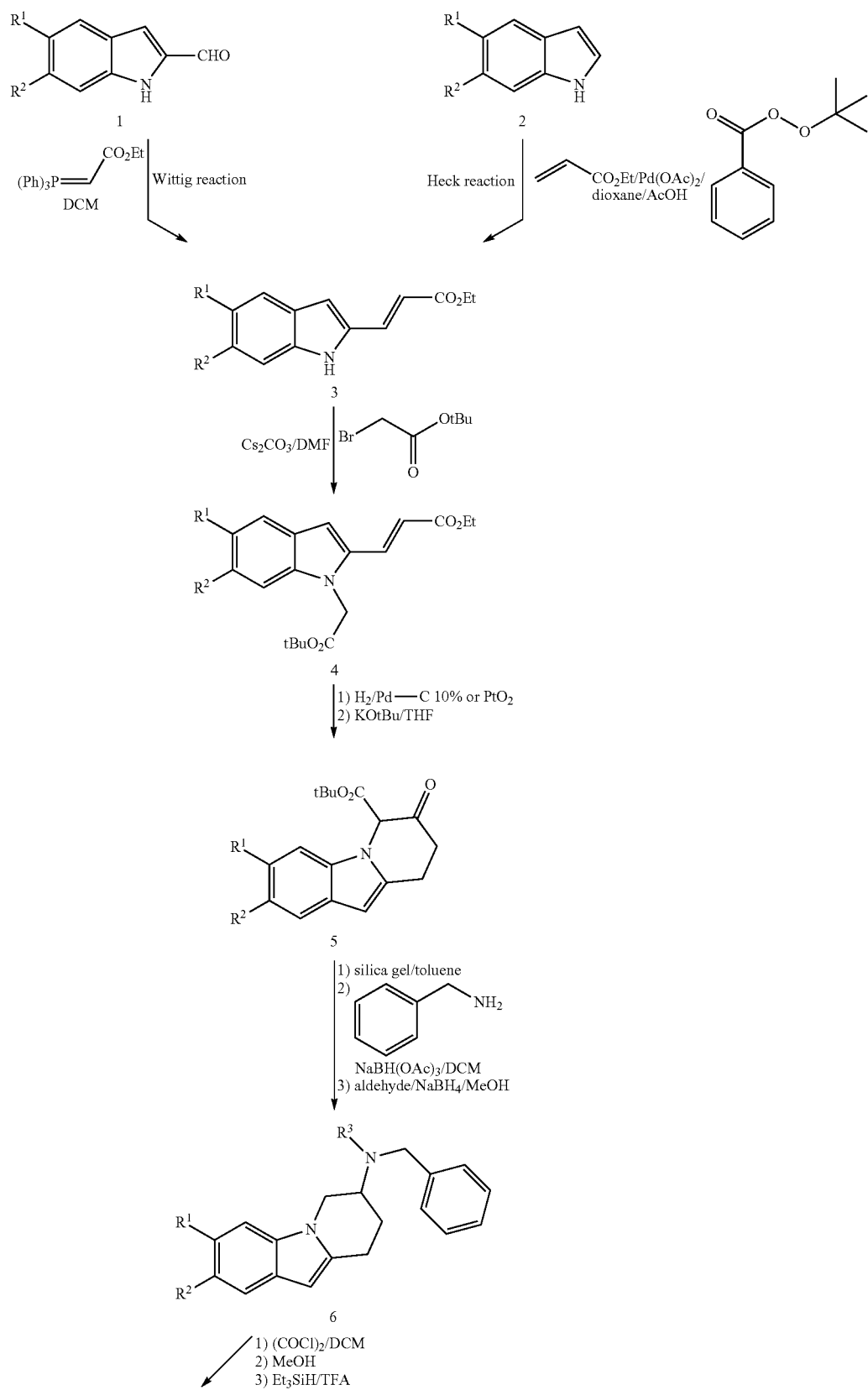

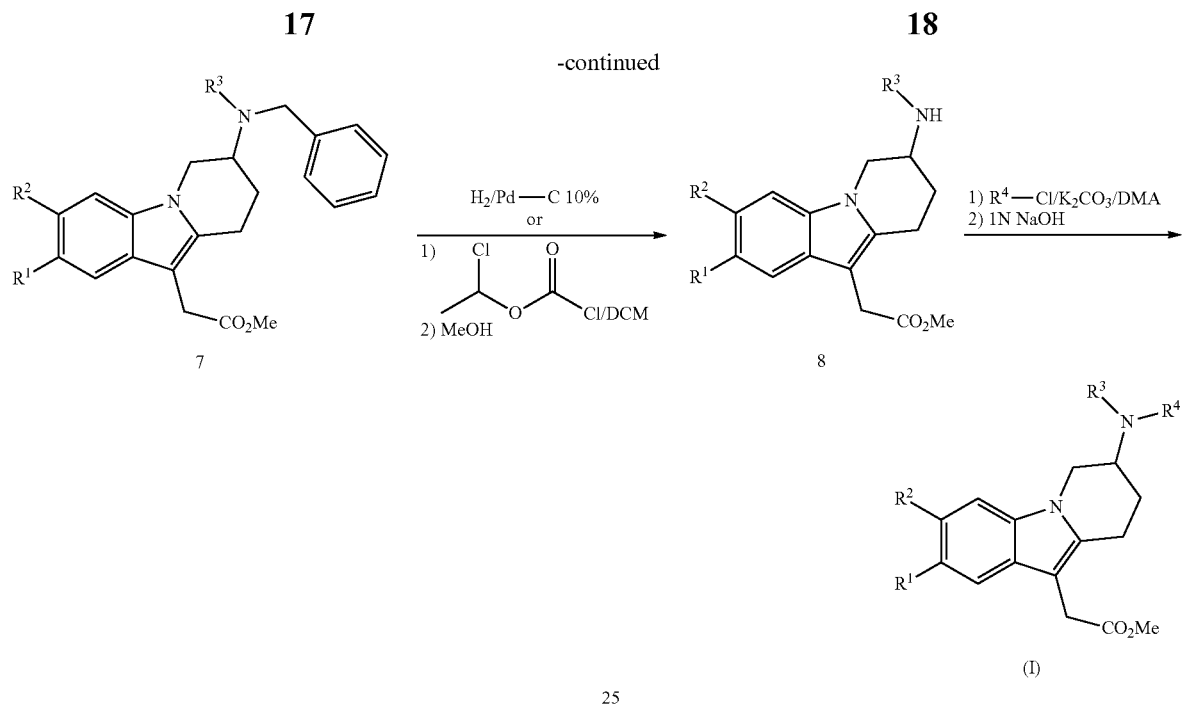

Compounds of formula (I) wherein $R^3$ represents hydrogen may be prepared from the respective tert-butyl 7-oxo-6,7,8,9-tetrahydropyrido[1,2-a]indole-6-carboxylate derivatives (5). Decarboxylation by reaction with silica gel in an aprotic solvent such as toluene gives the corresponding 8,9-dihydropyrido[1,2-a]indol-7(6H)-one derivatives (9). Reductive amination with ammonium acetate in the presence of a reducing agent such as $NaBH_3CN$ in a mixture of AcOH and EtOH and subsequent Boc protection yields the corresponding tert-butyl (6,7,8,9-tetrahydropyrido[1,2-a]indol-7-yl)carbamate derivatives (10). Friedel-Craft acylation by reaction with oxalyl chloride in an aprotic solvent such as DCM, followed by esterification with MeOH and subsequent reduction with triethylsilane in the presence of TFA gives the corresponding methyl 2-(7-amino-6,7,8,9-tetrahydropyrido[1,2-a]indol-10-yl)acetate (11). Reaction with an appropriate heteroaryl halide like $R^4$—Cl in the presence of a base such as $K_2CO_3$ in an aprotic solvent such as DMA and subsequent saponification with a base such as NaOH furnished the compounds of formula (I).

Scheme 2: General synthetic route for the preparation of compounds of formula (I)

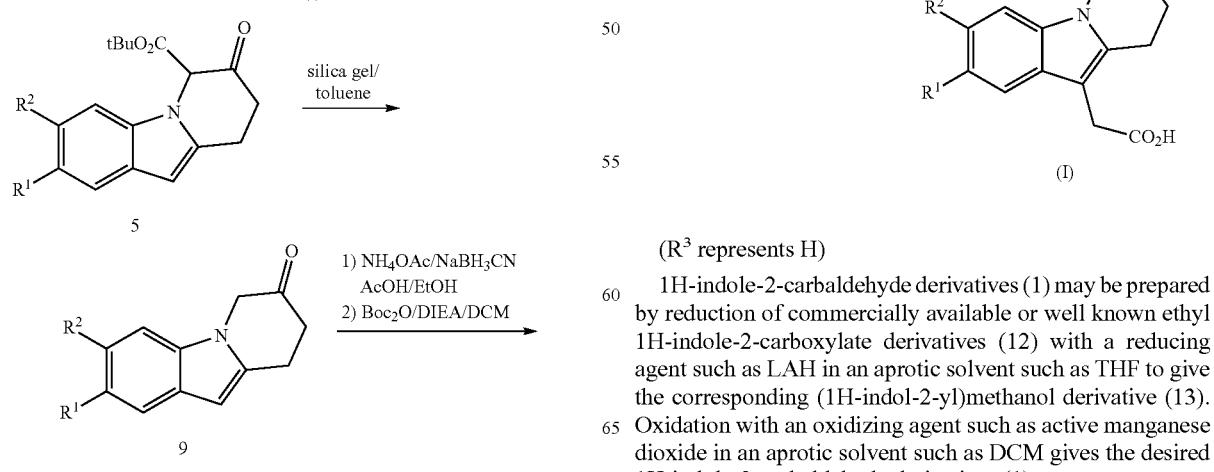

($R^3$ represents H)

1H-indole-2-carbaldehyde derivatives (1) may be prepared by reduction of commercially available or well known ethyl 1H-indole-2-carboxylate derivatives (12) with a reducing agent such as LAH in an aprotic solvent such as THF to give the corresponding (1H-indol-2-yl)methanol derivative (13). Oxidation with an oxidizing agent such as active manganese dioxide in an aprotic solvent such as DCM gives the desired 1H-indole-2-carbaldehyde derivatives (1).

Scheme 3: General synthetic route for the preparation of 1H-indole-2-carbaldehyde derivatives (1)

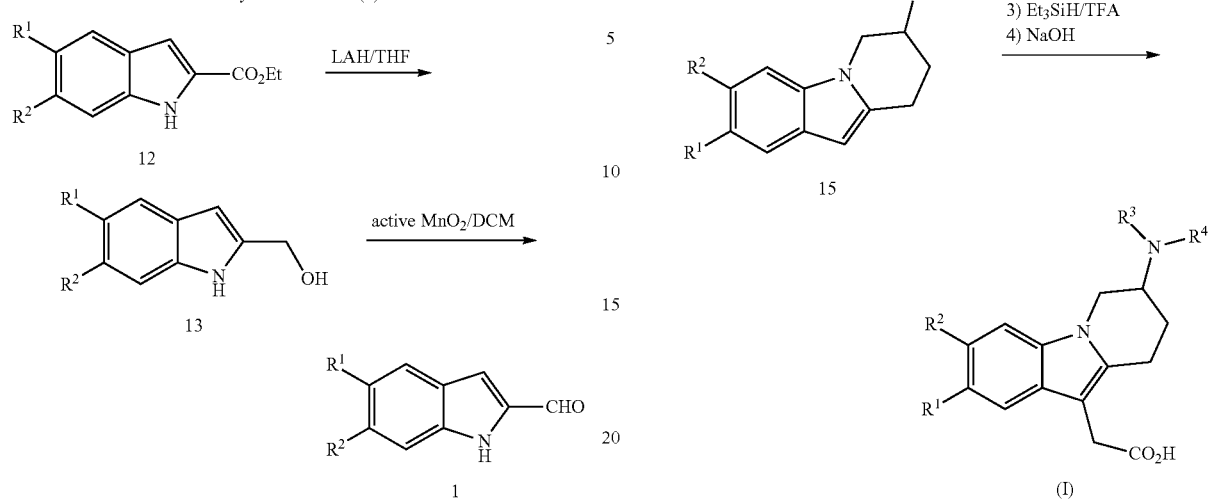

Compounds of formula (I) might also be prepared from the respective 8,9-dihydropyrido[1,2-a]indol-7(6H)-one derivatives (9). Reductive amination with ammonium acetate in the presence of a reducing agent such as $NaBH_3CN$ in a mixture of AcOH and EtOH yields the corresponding 6,7,8,9-tetrahydropyrido[1,2-a]indol-7-amine derivatives (14). Reaction with an appropriate heteroaryl halide like $R^4$—Cl in the presence of a base such as $K_2CO_3$ in an aprotic solvent such as DMA and subsequent alkylation with the respective $R^3$—X (with X=I, Br, OTf) in the presence of a strong base such as NaH in an aprotic solvent like DMA gives the desired 7-(Heteroaryl(alkyl)amino)-6,7,8,9-tetrahydropyrido[1,2-a]indole derivative (15). Friedel-Craft acylation by reaction with oxalyl chloride in an aprotic solvent such as DCM, followed by esterification with MeOH, reduction with triethylsilane in the presence of TFA and finally saponification with a base such as NaOH furnished the compounds of formula (I) (Method B).

Scheme 4: General synthetic route for the preparation of compounds of formula (I) (Method B)

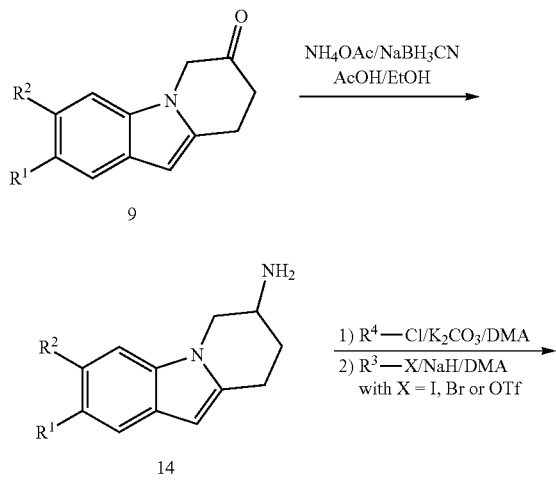

Whenever the compounds of formula (I) or an intermediate of structures 6 to 8, 10 or 15 are obtained in the form of mixtures of enantiomers, the enantiomers may be separated using methods known to the one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as TEA and/or diethylamine) and eluent B (hexane), at a flow rate of 0.8 to 150 mL/min.

Experimental Section

Abbreviations (as Used Herein)

Ac Acetyl
AcOH Acetic acid
aq. Aqueous
APC Allophycocyanin
Bdg Binding
Boc tert-butoxycarbonyl
BSA Bovine Serum Albumin
DCM Dichloromethane
DEA Diethylamine
DIEA N,N-Diisopropylethylamine
DMF Dimethylformamide
DMA Dimethylacetamide
DMSO Dimethylsulfoxide
dpm decays per minute
EA Ethyl acetate
EDTA Ethylene Diamine Tetraacetic Acid
Eq equivalent
ESI-MS Electrospray Ionization Mass Spectroscopy
Et Ethyl
EtOH Ethanol
FC Flash Chromatography
h Hour(s)
HEPES 4-(2-hydroxyethyl)-1-piperazineethanesulfonic acid
HPLC High Performance Liquid Chromatography
HSA Human Serum Albumin
iPr Isopropyl l Liter(s)
LAH Lithium aluminum hydride
LC-MS Liquid Chromatography-Mass Spectroscopy
Me Methyl
MeCN Acetonitrile
MeOH Methanol
min Minute(s)
MS Mass Spectroscopy
MW Microwave
N Normality of solution
PBS Phosphate Buffered Saline
PEI Polyethyleneimine
PG Protecting group
$PGD_2$ Prostaglandin $D_2$
Ph Phenyl
Pr Propyl
rt Room temperature
s Second(s)
sat Saturated
tBu tert-butyl
TEA Triethylamine
Tf Trifluoromethanesulfonyl
TFA Trifluoroacetic acid
THF Tetrahydrofuran
$t_R$ Retention time
Tris Tris-(hydroxymethyl)aminomethane buffer
Vol Volume Chemistry General Remarks All solvents and reagents are used as obtained from commercial sources unless otherwise indicated.

Temperatures are indicated in degrees Celsius (° C.). Unless otherwise indicated, the reactions take place at room temperature (rt).

In mixtures, relations of parts of solvent or eluent or reagent mixtures in liquid form are given as volume relations (v/v), unless indicated otherwise.

Analytical HPLC conditions as used in the Examples below:

HPLC/MS analyses are performed on a Agilent 1100 system, equipped with a Dionex P580 binary pump, a Dionex PDA-100 Photodiode Array Detector and a Finnigan AQA mass spectrometer (LC-1 and LC-2).

The LC retention times are obtained using the following elution conditions:

LC-1: Analytical HPLC on a Waters Atlantis T3 column (4.6×30 mm, 5 μm); Linear gradient of water/0.04% TFA (A) and MeCN (B) from 5% to 95% B over 1.5 min; flow rate 4.5 ml/min, detection at 210 nm.

LC-2: Analytical HPLC on a Zorbax® SB-AQ column (4.6×50 mm, 3.5 μm, Agilent); Linear gradient of water/0.04% TFA (A) and MeCN (B) from 5% to 95% B over 1.5 min; flow rate 4.5 ml/min, detection at 210 nm.

Preparative HPLC/MS purifications are performed on a Gilson 333/334 binary high pressure gradient pump system with a Gilson 215 autosampler and fraction collector, a Dionex UVD340U DAD detector, a polymerlabs PL-ELS 1000 ELS detector and a Finnigan AQA MS detector or a Thermo MSQ Plus MS detector, using a Waters Atlantis T3 column (10 μm, 30×75 mm), with a linear gradient of MeCN (A) and water/0.5% formic acid (B) over 5 min.; flow rate 75 ml/min.

Analytical HPLC over a chiral stationary phase are performed on a Daicel ChiralPak AD-H (4.6×250 mm, 5 μm) column. Typical conditions of chiral HPLC are an isocratic mixture of 50% heptane+0.05% DEA and 50% EtOH+0.05% DEA, at a flow rate of 0.8 mL/min., detection at 210 nm (chiral HPLC-1) or an isocratic mixture of 50% heptane and 50% EtOH+0.1% TFA, at a flow rate of 0.8 mL/min., detection at 210 nm (chiral HPLC-2).

Preparative HPLC over a chiral stationary phase are performed on a Daicel ChiralPak AD-H (20×250 mm, 5 μm) column. Typical conditions of chiral HPLC are an isocratic mixture of 50% EtOH and 50% hexane, at a flow rate of 16 mL/min., detection at 210 nm (chiral HPLC-3).

A. Synthesis of 7-(Heteroaryl-amino)-6,7,8,9-tetrahydropyrido[1,2-a]indol acetic acid derivatives (Method A)

A.1. Synthesis of ethyl 3-(1H-indol-2-yl)acrylate derivatives

General Procedure A (Via Wittig Reaction)

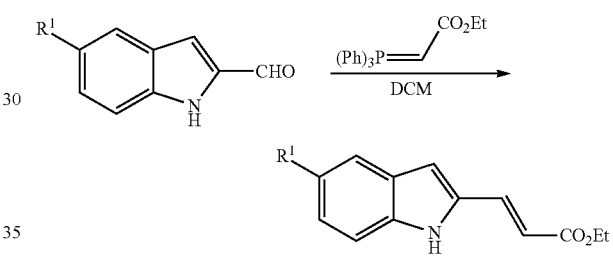

To a solution of the respective 1H-indole-2-carbaldehyde derivative (12 mmol) in DCM (135 ml) was added carbethoxymethylene triphenylphosphorane (12 mmol). The reaction mixture was stirred at rt for 16 h, concentrated in vacuo and the residue was purified by FC (EA/n-heptane: 0/10 to 3/7) to give the title compound as a solid.

The following (E)-ethyl 3-(1H-indol-2-yl)acrylate derivatives were synthetized according to the above general procedure

TABLE 1

| $R^1$ | Name | $[M + H]^+$ m/z | $t_R$ [min] LC-MS method |
|---|---|---|---|
| H | (E)-ethyl 3-(1H-indol-2-yl)acrylate | 216.02 | 0.91 LC-1 |
| Cl | (E)-ethyl 3-(5-chloro-1H-indol-2-yl)acrylate | 250.01 | 0.96 LC-1 |
| F | (E)-ethyl 3-(5-fluoro-1H-indol-2-yl)acrylate | 234.08 | 0.9 LC-1 |
| Me | (E)-ethyl 3-(5-methyl-1H-indol-2-yl)acrylate | 230.17 | 0.94 LC-1 |
| OMe | (E)-ethyl 3-(5-methoxy-1H-indol-2-yl)acrylate | 246.07 | 0.87 LC-1 |
| $OCF_3$ | (E)-ethyl 3-(5-(trifluoromethoxy)-1H-indol-2-yl)acrylate | 300.12 | 1.00 LC-1 |

General Procedure B (Via Heck Reaction)

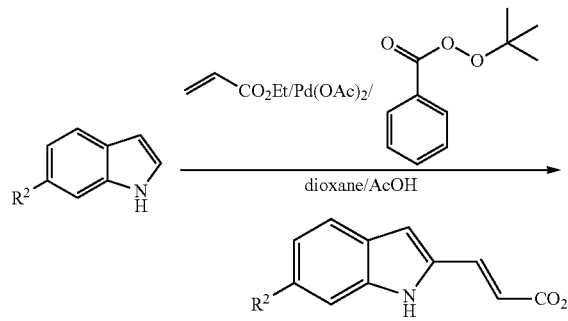

To a mixture of the respective indole derivative (14 mmol), ethyl acrylate (28 mmol), tert-butyl perbenzoate (12.6 mmol) in a mixture of dioxane (27 ml) and AcOH (9 ml) was added Pd(OAc)$_2$. The reaction mixture was stirred at 70° C. for 18 h. After cooling to rt, the reaction mixture was neutralized with sat. NaHCO$_3$ solution, diluted with EA and filtered over Celite. The organic extract was washed again with sat. NaHCO$_3$ solution, brine, dried over MgSO$_4$, filtered and concentrated in vacuo. The resulting residue was purified by FC (EA/n-heptane: 0/10 to 3/7) to give the title compound as a solid.

The following (E)-ethyl 3-(1H-indol-2-yl)acrylate derivatives were synthetized according to the above general procedure

TABLE 2

| R$^2$ | Name | [M + H]$^+$ m/z | t$_R$ [min] LC-MS method |
|---|---|---|---|
| Cl | (E)-ethyl 3-(6-chloro-1H-indol-2-yl)acrylate | 250.09 | 0.97 LC-1 |
| F | (E)-ethyl 3-(6-fluoro-1H-indol-2-yl)acrylate | 234.16 | 0.90 LC-1 |
| CF$_3$ | (E)-ethyl 3-(6-(trifluoromethyl)-1H-indol-2-yl)acrylate | 284.10 | 0.99 LC-1 |

A.2 Synthesis of (E)-ethyl 3-(1-(2-(tert-butoxy)-2-oxoethyl)-1H-indol-2-yl)acrylate derivatives

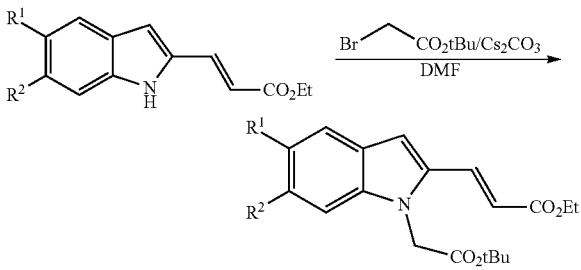

General Procedure

To a solution of the respective (E)-ethyl 3-(1H-indol-2-yl)acrylate derivative (26 mmol) in dry DMF (85 ml) were added tert-butyl bromoacetate (43 mmol) and Cs$_2$CO$_3$ (56 mmol). The reaction mixture was stirred at 60° C. for 20 h. After cooling to rt, the reaction mixture was diluted with acetone (85 ml) and filtered. The filtrate was concentrated in vacuo and the residue was purified by FC (EA/n-heptane: 0/10 to 2/8) to give the title compound as an oil.

The following (E)-ethyl 3-(1-(2-(tert-butoxy)-2-oxoethyl)-1H-indol-2-yl)acrylate derivatives were synthetized according to the above general procedure

TABLE 3

| R$^1$ | R$^2$ | Name | [M + H]$^+$ m/z | t$_R$ [min] LC-MS method |
|---|---|---|---|---|
| H | H | (E)-ethyl 3-(1-(2-(tert-butoxy)-2-oxoethyl)-1H-indol-2-yl)acrylate | 330.16 | 1.03 LC-1 |
| Cl | H | (E)-ethyl 3-(1-(2-(tert-butoxy)-2-oxoethyl)-5-chloro-1H-indol-2-yl)acrylate | 363.95 | 1.08 LC-1 |
| F | H | (E)-ethyl 3-(1-(2-(tert-butoxy)-2-oxoethyl)-5-fluoro-1H-indol-2-yl)acrylate | 348.07 | 1.03 LC-1 |
| Me | H | (E)-ethyl 3-(1-(2-(tert-butoxy)-2-oxoethyl)-5-methyl-1H-indol-2-yl)acrylate | 344.01 | 1.08 LC-1 |
| OMe | H | (E)-ethyl 3-(1-(2-(tert-butoxy)-2-oxoethyl)-5-methoxy-1H-indol-2-yl)acrylate | 360.11 | 1.01 LC-1 |
| OCF$_3$ | H | (E)-ethyl 3-(1-(2-(tert-butoxy)-2-oxoethyl)-5-(trifluoromethoxy)-1H-indol-2-yl)acrylate | 413.94 | 1.1 LC-1 |
| H | Cl | (E)-ethyl 3-(1-(2-(tert-butoxy)-2-oxoethyl)-6-chloro-1H-indol-2-yl)acrylate | 363.88 | 1.09 LC-1 |
| H | F | (E)-ethyl 3-(1-(2-(tert-butoxy)-2-oxoethyl)-6-fluoro-1H-indol-2-yl)acrylate | 348.10 | 1.04 LC-1 |
| H | CF$_3$ | (E)-ethyl 3-(1-(2-(tert-butoxy)-2-oxoethyl)-6-(trifluoromethyl)-1H-indol-2-yl)acrylate | 397.99 | 1.1 LC-1 |

A.3 Synthesis of tert-butyl 7-oxo-6,7,8,9-tetrahydropyrido[1,2-a]indole-6-carboxylate derivatives

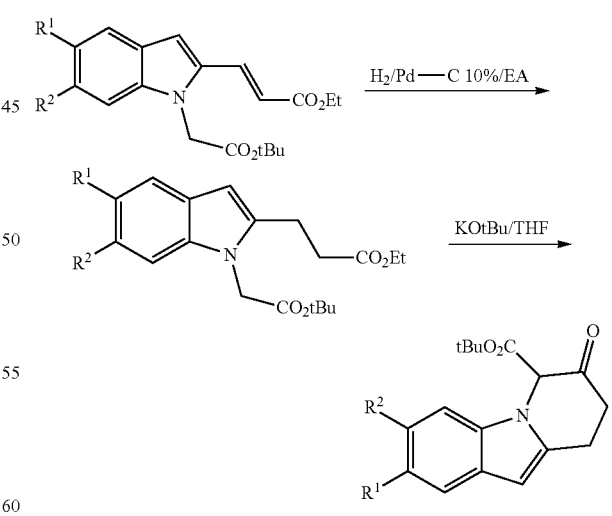

General Procedure

A suspension of the respective (E)-ethyl 3-(1-(2-(tert-butoxy)-2-oxoethyl)-1H-indol-2-yl)acrylate derivative (8.5 mmol), Pd—C 10% (300 mg) in EA (28 ml) was stirred under hydrogen atmosphere for 2 h at rt. The reaction was then filtered over celite to give the crude diester which was used for the next step without further purification. To a cold (−10° C.) solution of the crude diester (8.5 mmol) in dry THF (22.5 ml) was added dropwise a solution of potassium tert-butoxide (8.5 mmol) in dry THF (112.5 ml). The reaction mixture was allowed to stir at rt for 10 min., quenched with HCl 1N (12 ml) and extracted with n-hexane. The combined organic extracts were dried over MgSO$_4$, filtered and concentrated in vacuo. The resulting residue was purified by FC (EN n-heptane: 0/10 to 1/9) to give the title compound as an oil.

The following tert-butyl 7-oxo-6,7,8,9-tetrahydropyrido[1,2-a]indole-6-carboxylate derivatives were synthetized according to the above general procedure, except for tert-butyl 3-chloro-7-oxo-6,7,8,9-tetrahydropyrido[1,2-a]indole-6-carboxylate where Pd—C 10% was replaced by PtO$_2$ hydrate.

TABLE 4

| $R^1$ | $R^2$ | Name | $[M + H]^+$ m/z | $t_R$ [min] LC-MS method |
|---|---|---|---|---|
| H | H | tert-butyl 7-oxo-6,7,8,9-tetrahydropyrido[1,2-a]indole-6-carboxylate | 286.16 | 0.96 LC-1 |
| Cl | H | tert-butyl 2-chloro-7-oxo-6,7,8,9-tetrahydropyrido[1,2-a]indole-6-carboxylate | 320.08 | 1.02 LC-1 |
| F | H | tert-butyl 2-fluoro-7-oxo-6,7,8,9-tetrahydropyrido[1,2-a]indole-6-carboxylate | 304.05 | 0.97 LC-1 |
| Me | H | tert-butyl 2-methyl-7-oxo-6,7,8,9-tetrahydropyrido[1,2-a]indole-6-carboxylate | 300.12 | 1.01 LC-1 |
| OMe | H | tert-butyl 2-methoxy-7-oxo-6,7,8,9-tetrahydropyrido[1,2-a]indole-6-carboxylate | 316.11 | 0.94 LC-1 |
| OCF$_3$ | H | tert-butyl 7-oxo-2-(trifluoromethoxy)-6,7,8,9-tetrahydropyrido[1,2-a]indole-6-carboxylate | 369.83 | 1.05 LC-1 |
| H | Cl | tert-butyl 3-chloro-7-oxo-6,7,8,9-tetrahydropyrido[1,2-a]indole-6-carboxylate | 320.05 | 1.02 LC-1 |
| H | F | tert-butyl 3-fluoro-7-oxo-6,7,8,9-tetrahydropyrido[1,2-a]indole-6-carboxylate | 304.07 | 0.97 LC-1 |
| H | CF$_3$ | tert-butyl 7-oxo-3-(trifluoromethyl)-6,7,8,9-tetrahydropyrido[1,2-a]indole-6-carboxylate | 353.78 | 1.03 LC-1 |

A.4 Synthesis of 8,9-dihydropyrido[1,2-a]indol-7(6H)-one derivatives

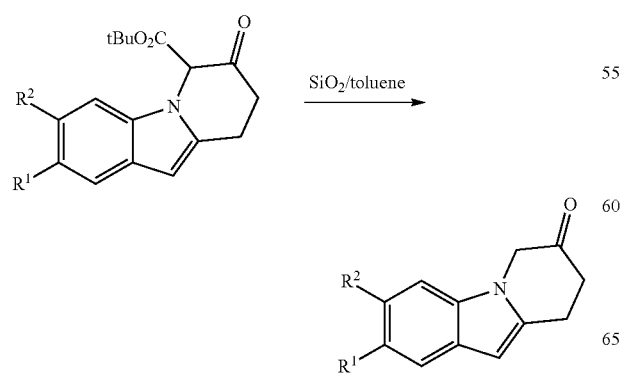

General Procedure

A mixture of the respective tert-butyl 7-oxo-6,7,8,9-tetrahydropyrido[1,2-a]indole-6-carboxylate derivative (5.3 mmol) and silica gel (7 g) in toluene (70 ml) was stirred at reflux for 6 h and allowed to stir at rt overnight. The reaction mixture was then filtered, the solid was washed with EA and the filtrate was concentrated in vacuo to give the title compound which was used for the next step without further purification.

The following 8,9-dihydropyrido[1,2-a]indol-7(6H)-one derivatives were synthetized according to the above general procedure.

TABLE 5

| $R^1$ | $R^2$ | Name | $[M + H]^+$ m/z | $t_R$ [min] LC-MS method |
|---|---|---|---|---|
| H | H | 8,9-dihydropyrido[1,2-a]indol-7(6H)-one | 186.23 | 0.79 LC-1 |
| Cl | H | 2-chloro-8,9-dihydropyrido[1,2-a]indol-7(6H)-one | 220.01 | 0.87 LC-1 |
| F | H | 2-fluoro-8,9-dihydropyrido[1,2-a]indol-7(6H)-one | 204.15 | 0.82 LC-1 |
| Me | H | 2-methyl-8,9-dihydropyrido[1,2-a]indol-7(6H)-one | 200.19 | 0.86 LC-1 |
| OMe | H | 2-methoxy-8,9-dihydropyrido[1,2-a]indol-7(6H)-one | 216.14 | 0.77 LC-1 |
| OCF$_3$ | H | 2-(trifluoromethoxy)-8,9-dihydropyrido[1,2-a]indol-7(6H)-one | 270.08 | 0.93 LC-1 |
| H | Cl | 3-chloro-8,9-dihydropyrido[1,2-a]indol-7(6H)-one | 220.08 | 0.88 LC-1 |
| H | F | 3-fluoro-8,9-dihydropyrido[1,2-a]indol-7(6H)-one | 204.18 | 0.82 LC-1 |
| H | CF$_3$ | 3-(trifluoromethyl)-8,9-dihydropyrido[1,2-a]indol-7(6H)-one | 254.03 | 0.91 LC-1 |

A.5 Synthesis of N-benzyl-6,7,8,9-tetrahydropyrido[1,2-a]indol-7-amine derivatives

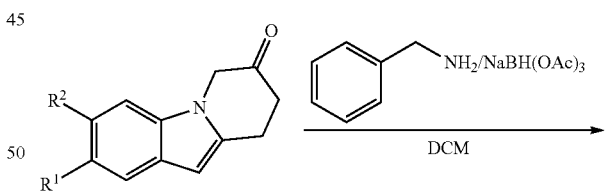

General Procedure

To a solution of the respective 8,9-dihydropyrido[1,2-a]indol-7(6H)-one derivative (2.7 mmol) in dry DCM (20 ml) were added successively benzylamine (3 mmol) and NaBH (OAc)₃ (2.7 mmol). The resulting reaction mixture was stirred at rt for 1 h and then quenched with sat. NaHCO₃ solution. The aqueous phase was extracted with DCM, the combined organic extracts were washed with water, brine, dried over MgSO₄, filtered and concentrated in vacuo. The resulting residue was purified by FC (EA/n-heptane: 0/10 to 3/7) to give the title compound as an oil.

The following N-benzyl-6,7,8,9-tetrahydropyrido[1,2-a]indol-7-amine derivatives were synthetized according to the above general procedure.

TABLE 6

| R¹ | R² | Name | [M + H]⁺ m/z | $t_R$ [min] LC-MS method |
|---|---|---|---|---|
| H | H | N-benzyl-6,7,8,9-tetrahydropyrido[1,2-a]indol-7-amine | 277.15 | 0.62 LC-1 |
| Cl | H | N-benzyl-2-chloro-6,7,8,9-tetrahydropyrido[1,2-a]indol-7-amine | 311.06 | 0.68 LC-1 |
| F | H | N-benzyl-2-fluoro-6,7,8,9-tetrahydropyrido[1,2-a]indol-7-amine | 295.11 | 0.63 LC-1 |
| Me | H | N-benzyl-2-methyl-6,7,8,9-tetrahydropyrido[1,2-a]indol-7-amine | 291.21 | 0.66 LC-1 |
| OMe | H | N-benzyl-2-methoxy-6,7,8,9-tetrahydropyrido[1,2-a]indol-7-amine | 307.16 | 0.60 LC-1 |
| OCF₃ | H | N-benzyl-2-(trifluoromethoxy)-6,7,8,9-tetrahydropyrido[1,2-a]indol-7-amine | 360.99 | 0.72 LC-1 |
| H | Cl | N-benzyl-3-chloro-6,7,8,9-tetrahydropyrido[1,2-a]indol-7-amine | 311.10 | 0.68 LC-1 |
| H | F | N-benzyl-3-fluoro-6,7,8,9-tetrahydropyrido[1,2-a]indol-7-amine | 295.11 | 0.64 LC-1 |
| H | CF₃ | N-benzyl-3-(trifluoromethyl)-6,7,8,9-tetrahydropyrido[1,2-a]indol-7-amine | 344.96 | 0.72 LC-1 |

A.6 Synthesis of N-benzyl-N-alkyl-6,7,8,9-tetrahydropyrido[1,2-a]indol-7-amine derivatives

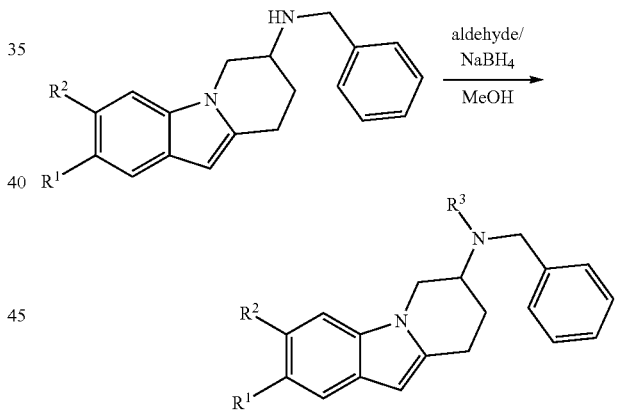

General Procedure

To a cold (0° C.) solution of the respective N-benzyl-6,7,8,9-tetrahydropyrido[1,2-a]indol-7-amine derivative (2 mmol) and formaldehyde (36.5% in water, 10 mmol) in dry MeOH (20 ml) was added portionwise over 20 min. NaBH₄ (6 mmol). The resulting reaction was allowed to warm-up to rt and stirred overnight. The reaction mixture was then poured into water and extracted with EA. The combined organic extracts were washed with brine, dried over MgSO₄, filtered and concentrated in vacuo to give the title compound as an oil which was used for the next step without further purification.

The following N-benzyl-N-alkyl-6,7,8,9-tetrahydropyrido[1,2-a]indol-7-amine derivatives were synthetized according to the above general procedure.

TABLE 7

| R¹ | R² | R³ | Name | [M + H]⁺ m/z | $t_R$ [min] LC-MS method |
|---|---|---|---|---|---|
| H | H | Me | N-benzyl-N-methyl-6,7,8,9-tetrahydropyrido[1,2-a]indol-7-amine | 291.35 | 0.73 LC-2 |
| Cl | H | Me | N-benzyl-2-chloro-N-methyl-6,7,8,9-tetrahydropyrido[1,2-a]indol-7-amine | 325.17 | 0.65 LC-1 |
| F | H | Me | N-benzyl-2-fluoro-N-methyl-6,7,8,9-tetrahydropyrido[1,2-a]indol-7-amine | 309.11 | 0.68 LC-1 |
| Me | H | Me | N-benzyl-N,2-dimethyl-6,7,8,9-tetrahydropyrido[1,2-a]indol-7-amine | 305.22 | 0.68 LC-1 |
| OMe | H | Me | N-benzyl-2-methoxy-N-methyl-6,7,8,9-tetrahydropyrido[1,2-a]indol-7-amine | 321.17 | 0.62 LC-1 |
| OCF₃ | H | Me | N-benzyl-N-methyl-2-(trifluoromethoxy)-6,7,8,9-tetrahydropyrido[1,2-a]indol-7-amine | 375.14 | 0.75 LC-1 |
| H | Cl | Me | N-benzyl-3-chloro-N-methyl-6,7,8,9-tetrahydropyrido[1,2-a]indol-7-amine | 325.06 | 0.71 LC-1 |
| H | F | Me | N-benzyl-3-fluoro-N-methyl-6,7,8,9-tetrahydropyrido[1,2-a]indol-7-amine | 309.12 | 0.66 LC-1 |
| H | CF₃ | Me | N-benzyl-N-methyl-3-(trifluoromethyl)-6,7,8,9-tetrahydropyrido[1,2-a]indol-7-amine | 358.85 | 0.74 LC-1 |

A.7 Synthesis of methyl 2-(7-(benzyl(alkyl)amino)-6,7,8,9-tetrahydropyrido[1,2-a]indol-10-yl)-2-oxoacetate derivatives

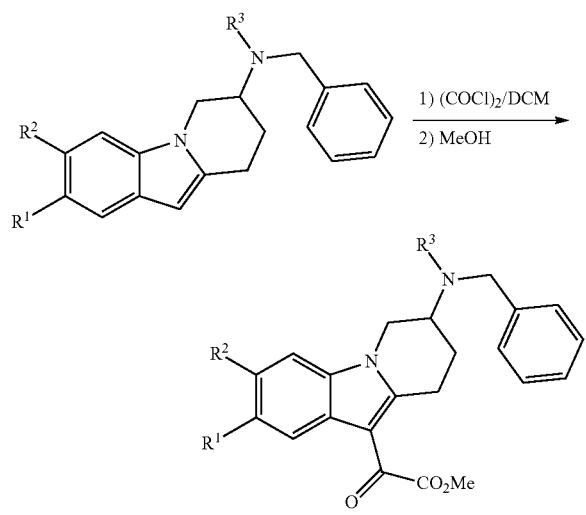

General Procedure

To a cold (0° C.) solution of the respective N-benzyl-N-alkyl-6,7,8,9-tetrahydropyrido[1,2-a]indol-7-amine derivative (2 mmol) in dry DCM (40 ml) was added oxalyl chloride (4 mmol). After stirring at 0° C. for 1 h, MeOH (3 ml) was added and the reaction mixture was stirred at 0° C. for 1 h, quenched with sat.NaHCO₃ solution. The aqueous phase was extracted with DCM, the combined extracts were dried over MgSO₄, filtered and concentrated in vacuo to give the title compound as an oil which was used for the next step without further purification.

The following methyl 2-(7-(benzyl(alkyl)amino)-6,7,8,9-tetrahydropyrido[1,2-a]indol-10-yl)-2-oxoacetate derivatives were synthetized according to the above general procedure.

TABLE 8

| R¹ | R² | R³ | Name | [M + H]⁺ m/z | $t_R$ [min] LC-MS method |
|---|---|---|---|---|---|
| H | H | Me | methyl 2-(7-(benzyl(methyl)amino)-6,7,8,9-tetrahydropyrido[1,2-a]indol-10-yl)-2-oxoacetate | 377.34 | 0.70 LC-2 |
| Cl | H | Me | methyl 2-(7-(benzyl(methyl)amino)-2-chloro-6,7,8,9-tetrahydropyrido[1,2-a]indol-10-yl)-2-oxoacetate | 411.08 | 0.66 LC-1 |
| F | H | Me | methyl 2-(7-(benzyl(methyl)amino)-2-fluoro-6,7,8,9-tetrahydropyrido[1,2-a]indol-10-yl)-2-oxoacetate | 394.88 | 0.63 LC-1 |
| Me | H | Me | methyl 2-(7-(benzyl(methyl)amino)-2-methyl-6,7,8,9-tetrahydropyrido[1,2-a]indol-10-yl)-2-oxoacetate | 391.14 | 0.63 LC-1 |
| OMe | H | Me | methyl 2-(7-(benzyl(methyl)amino)-2-methoxy-6,7,8,9-tetrahydropyrido[1,2-a]indol-10-yl)-2-oxoacetate | 407.04 | 0.61 LC-1 |
| OCF₃ | H | Me | methyl 2-(7-(benzyl(methyl)amino)-2-(trifluoromethoxy)-6,7,8,9-tetrahydropyrido[1,2-a]indol-10-yl)-2-oxoacetate | 460.96 | 0.72 LC-1 |

TABLE 8-continued

| $R^1$ | $R^2$ | $R^3$ | Name | $[M + H]^+$ m/z | $t_R$ [min] LC-MS method |
|---|---|---|---|---|---|
| H | Cl | Me | methyl 2-(7-(benzyl(methyl)amino)-3-chloro-6,7,8,9-tetrahydropyrido[1,2-a]indol-10-yl)-2-oxoacetate | 411.07 | 0.69 LC-1 |
| H | F | Me | methyl 2-(7-(benzyl(methyl)amino)-3-fluoro-6,7,8,9-tetrahydropyrido[1,2-a]indol-10-yl)-2-oxoacetate | 395.02 | 0.64 LC-1 |
| H | $CF_3$ | Me | methyl 2-(7-(benzyl(methyl)amino)-3-(trifluoromethyl)-6,7,8,9-tetrahydropyrido[1,2-a]indol-10-yl)-2-oxoacetate | 445.13 | 0.72 LC-1 |

A.8 Synthesis of methyl 2-(7-(benzyl(alkyl)amino)-6,7,8,9-tetrahydropyrido[1,2-a]indol-10-yl)acetate derivatives

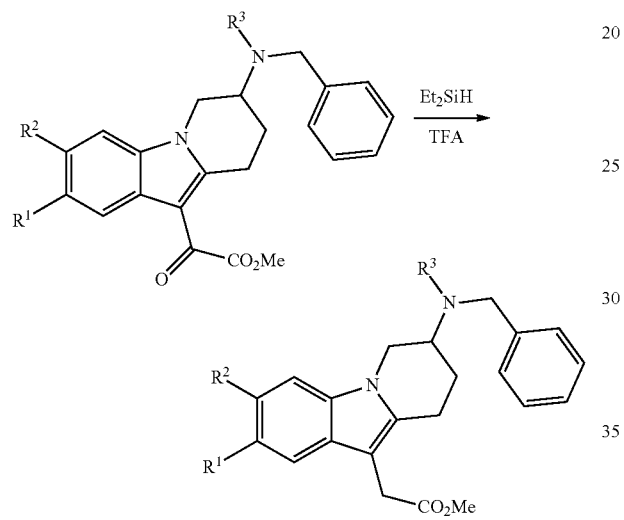

General Procedure

To a solution of the respective methyl 2-(7-(benzyl(alkyl)amino)-6,7,8,9-tetrahydropyrido[1,2-a]indol-10-yl)-2-oxoacetate (1 mmol) in TFA (11 ml) was added triethylsilane (2 mmol). The reaction mixture was stirred at rt for 2 h and concentrated in vacuo. The resulting residue was dissolved in EA, washed with sat.NaHCO$_3$ solution, water, brine, dried over MgSO$_4$, filtered and concentrated in vacuo. The resulting residue was purified by FC (EN n-heptane: 0/10 to 3/7) to give the title compound as a solid.

The following methyl 2-(7-(benzyl(alkyl)amino)-6,7,8,9-tetrahydropyrido[1,2-a]indol-10-yl)acetate derivatives were synthetized according to the above general procedure.

TABLE 9

| $R^1$ | $R^2$ | $R^3$ | Name | $[M + H]^+$ m/z | $t_R$ [min] LC-MS method |
|---|---|---|---|---|---|
| H | H | Me | methyl 2-(7-(benzyl(methyl)amino)-6,7,8,9-tetrahydropyrido[1,2-a]indol-10-yl)acetate | 363.35 | 0.73 LC-2 |
| Cl | H | Me | methyl 2-(7-(benzyl(methyl)amino)-2-chloro-6,7,8,9-tetrahydropyrido[1,2-a]indol-10-yl)acetate | 396.96 | 0.69 LC-1 |
| F | H | Me | methyl 2-(7-(benzyl(methyl)amino)-2-fluoro-6,7,8,9-tetrahydropyrido[1,2-a]indol-10-yl)acetate | 381.08 | 0.65 LC-1 |
| Me | H | Me | methyl 2-(7-(benzyl(methyl)amino)-2-methyl-6,7,8,9-tetrahydropyrido[1,2-a]indol-10-yl)acetate | 376.97 | 0.67 LC-1 |
| OMe | H | Me | methyl 2-(7-(benzyl(methyl)amino)-2-methoxy-6,7,8,9-tetrahydropyrido[1,2-a]indol-10-yl)acetate | 393.11 | 0.63 LC-1 |
| $OCF_3$ | H | Me | methyl 2-(7-(benzyl(methyl)amino)-2-(trifuoromethoxy)-6,7,8,9-tetrahydropyrido[1,2-a]indol-10-yl)acetate | 446.96 | 0.73 LC-1 |
| H | Cl | Me | methyl 2-(7-(benzyl(methyl)amino)-3-chloro-6,7,8,9-tetrahydropyrido[1,2-a]indol-10-yl)acetate | 396.72 | 0.70 LC-1 |
| H | F | Me | methyl 2-(7-(benzyl(methyl)amino)-3-fluoro-6,7,8,9-tetrahydropyrido[1,2-a]indol-10-yl)acetate | 381.04 | 0.66 LC-1 |
| H | $CF_3$ | Me | N-benzyl-N-methyl-3-(trifluoromethyl)-6,7,8,9-tetrahydropyrido[1,2-a]indol-7-amine | 430.96 | 0.73 LC-1 |

A.9 Synthesis of methyl 2-(7-(alkylamino)-6,7,8,9-tetrahydropyrido[1,2-a]indol-10-yl)acetate derivatives

General Procedure A (Via Hydrogenation Over Pd—C 10%)

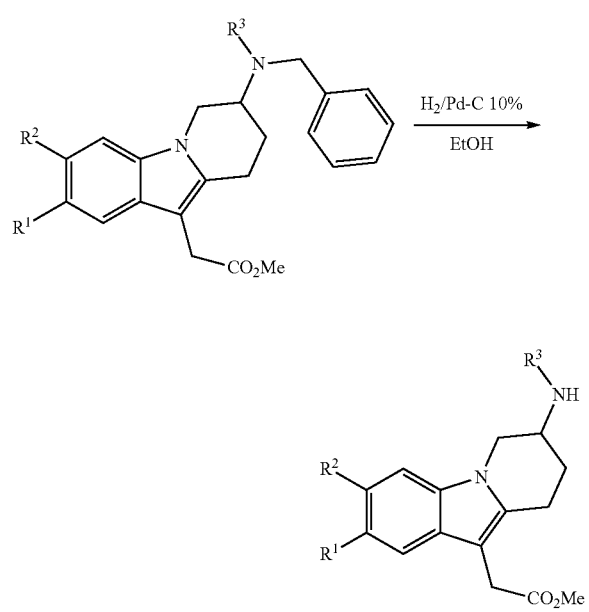

A mixture of the respective methyl 2-(7-(benzyl(alkyl)amino)-6,7,8,9-tetrahydropyrido[1,2-a]indol-10-yl)acetate derivative (1 mmol) and Pd—C 10% (60 mg) in MeOH (30 ml) was stirred under hydrogen atmosphere for 12 h. The reaction mixture was filtered over celite, and the filtrate was concentrated in vacuo to give the title compound as an oil which was used for the next step without further purification.

The following methyl 2-(7-(alkylamino)-6,7,8,9-tetrahydropyrido[1,2-a]indol-10-yl)acetate derivatives were synthetized according to the above general procedure.

General Procedure B (Via Reaction with 1-Chloroethyl Chloroformate)

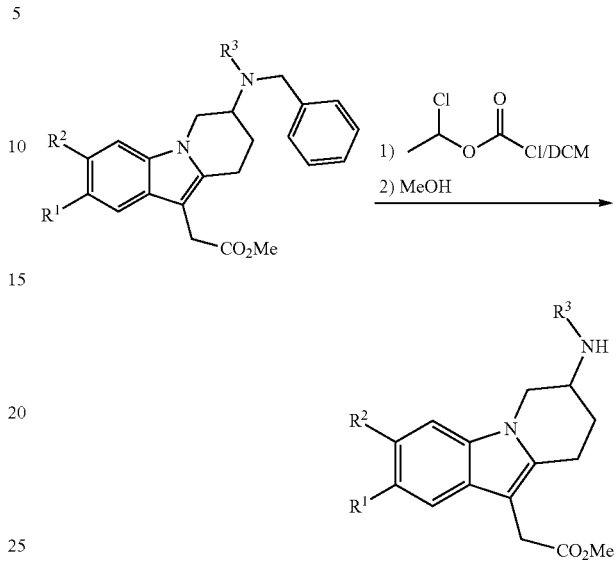

To a solution of the respective methyl 2-(7-(benzyl(alkyl)amino)-6,7,8,9-tetrahydropyrido[1,2-a]indol-10-yl)acetate derivative (1 mmol) in dry DCM (15 ml) in a sealed tube, was added 1-chloroethyl chloroformate (2 mmol). The reaction mixture was stirred at 80° C. for 12 h. After cooling to rt, the reaction mixture was concentrated in vacuo. To the residue was added MeOH (15 ml), the reaction mixture was stirred at reflux for 1 h and concentrated in vacuo. The residue was dissolved in EA and washed with sat. NaHCO$_3$ solution. The aqueous phase was extracted with EA, the combined extracts were dried over MgSO$_4$, filtered and concentrated in vacuo. The resulting residue was purified by FC (DCM/MeOH: 10/0 to 9/1) to give the title compound as an oil.

The following methyl 2-(7-(alkylamino)-6,7,8,9-tetrahydropyrido[1,2-a]indol-10-yl)acetate derivatives were synthetized according to the above general procedure.

TABLE 10

| $R^1$ | $R^2$ | $R^3$ | Name | $[M + H]^+$ m/z | $t_R$ [min] LC-MS method |
|---|---|---|---|---|---|
| H | H | Me | methyl 2-(7-(methylamino)-6,7,8,9-tetrahydropyrido[1,2-a]indol-10-yl)acetate | 273.15 | 0.6 LC-2 |
| F | H | Me | methyl 2-(2-fluoro-7-(methylamino)-6,7,8,9-tetrahydropyrido[1,2-a]indol-10-yl)acetate | 291.03 | 0.55 LC-1 |
| Me | H | Me | methyl 2-(2-methyl-7-(methylamino)-6,7,8,9-tetrahydropyrido[1,2-a]indol-10-yl)acetate | 287.16 | 0.57 LC-1 |
| OMe | H | Me | methyl 2-(2-methoxy-7-(methylamino)-6,7,8,9-tetrahydropyrido[1,2-a]indol-10-yl)acetate | 303.07 | 0.51 LC-1 |
| OCF$_3$ | H | Me | methyl 2-(7-(methylamino)-2-(trifluoromethoxy)-6,7,8,9-tetrahydropyrido[1,2-a]indol-10-yl)acetate | 357 | 0.64 LC-1 |
| H | F | Me | methyl 2-(3-fluoro-7-(methylamino)-6,7,8,9-tetrahydropyrido[1,2-a]indol-10-yl)acetate | 290.89 | 0.55 LC-1 |
| H | CF$_3$ | Me | methyl 2-(7-(methylamino)-3-(trifluoromethyl)-6,7,8,9-tetrahydropyrido[1,2-a]indol-10-yl)acetate | 341.09 | 0.63 LC-1 |

TABLE 11

| $R^1$ | $R^2$ | $R^3$ | Name | $[M+H]^+$ m/z | $t_R$ [min] LC-MS method |
|---|---|---|---|---|---|
| Cl | H | Me | methyl 2-(2-chloro-7-(methylamino)-6,7,8,9-tetrahydropyrido[1,2-a]indol-10-yl)acetate | 307.12 | 0.58 LC-1 |
| H | Cl | Me | methyl 2-(3-chloro-7-(methylamino)-6,7,8,9-tetrahydropyrido[1,2-a]indol-10-yl)acetate | 306.96 | 0.59 LC-1 |

A.10 Synthesis of 7-(Heteroaryl(alkyl)amino)-6,7,8,9-tetrahydropyrido[1,2-a]indol acetic acid derivatives

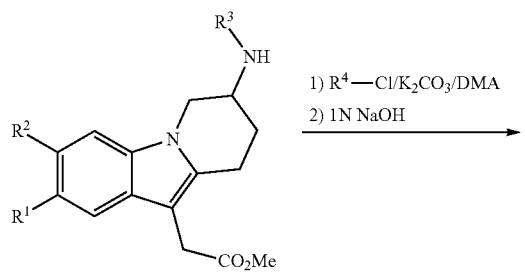

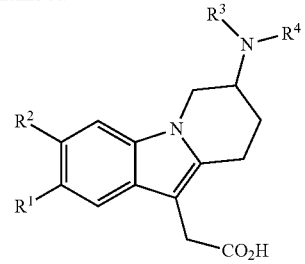

General Procedure

A mixture of the respective methyl 2-(7-(alkylamino)-6,7,8,9-tetrahydropyrido[1,2-a]indol-10-yl)acetate derivative (1 mmol), the appropriate $R^4$—Cl (1 mmol) and $K_2CO_3$ (1.5 mmol) in DMA (20 ml) was stirred at 130° C. for 12 h. After cooling to rt, 1N NaOH (20 ml) was added to the reaction mixture. The reaction mixture was stirred at rt for 2 h and then 37% HCl was added until pH 1-2. The products were directly purified by prep. HPLC to provide the final compound.

Preparation of Examples

The following 7-(Heteroaryl(alkyl)amino)-6,7,8,9-tetrahydropyrido[1,2-a]indol acetic acid derivatives were synthetized according to the above general procedure.

TABLE 12

| Example | Name | $[M+H]^+$ m/z | $t_R$ [min.] LC-MS method |
|---|---|---|---|
| 1 | 2-(7-((5-chloropyrimidin-2-yl)(methyl)amino)-6,7,8,9-tetrahydropyrido[1,2-a]indol-10-yl)acetic acid | 370.97 | 0.93 LC-1 |
| 2 | 2-(7-((5-fluoropyrimidin-2-yl)(methyl)amino)-6,7,8,9-tetrahydropyrido[1,2-a]indol-10-yl)acetic acid | 355.05 | 0.86 LC-1 |
| 3 | 2-(7-(methyl(5-(trifluoromethyl)pyrimidin-2-yl)amino)-6,7,8,9-tetrahydropyrido[1,2-a]indol-10-yl)acetic acid | 405.02 | 0.95 LC-1 |
| 4 | 2-(7-((6-fluorobenzo[d]thiazol-2-yl)(methyl)amino)-6,7,8,9-tetrahydropyrido[1,2-a]indol-10-yl)acetic acid | 410 | 0.89 LC-1 |
| 5 | 2-(7-((5-fluorobenzo[d]oxazol-2-yl)(methyl)amino)-6,7,8,9-tetrahydropyrido[1,2-a]indol-10-yl)acetic acid | 394.06 | 0.86 LC-1 |
| 6 | 2-(7-((5-fluorobenzo[d]thiazol-2-yl)(methyl)amino)-6,7,8,9-tetrahydropyrido[1,2-a]indol-10-yl)acetic acid | 410 | 0.91 LC-1 |
| 7 | 2-(2-fluoro-7-((5-fluoropyrimidin-2-yl)(methyl)amino)-6,7,8,9-tetrahydropyrido[1,2-a]indol-10-yl)acetic acid | 372.95 | 0.88 LC-1 |
| 8 | 2-(2-fluoro-7-((5-fluorobenzo[d]oxazol-2-yl)(methyl)amino)-6,7,8,9-tetrahydropyrido[1,2-a]indol-10-yl)acetic acid | 412.07 | 0.88 LC-1 |
| 9 | 2-(3-fluoro-7-((5-fluoropyrimidin-2-yl)(methyl)amino)-6,7,8,9-tetrahydropyrido[1,2-a]indol-10-yl)acetic acid | 373.05 | 0.88 LC-1 |
| 10 | 2-(3-fluoro-7-((5-fluorobenzo[d]oxazol-2-yl)(methyl)amino)-6,7,8,9-tetrahydropyrido[1,2-a]indol-10-yl)acetic acid | 412.07 | 0.88 LC-1 |
| 11 | 2-(7-((5-fluoropyrimidin-2-yl)(methyl)amino)-2-methoxy-6,7,8,9-tetrahydropyrido[1,2-a]indol-10-yl)acetic acid | 384.99 | 0.85 LC-1 |
| 12 | 2-(7-((5-fluorobenzo[d]oxazol-2-yl)(methyl)amino)-2-methoxy-6,7,8,9-tetrahydropyrido[1,2-a]indol-10-yl)acetic acid | 424.08 | 0.85 LC-1 |
| 13 | 2-(7-((5-fluoropyrimidin-2-yl)(methyl)amino)-2-methyl-6,7,8,9-tetrahydropyrido[1,2-a]indol-10-yl)acetic acid | 368.94 | 0.91 LC-1 |

TABLE 12-continued

| Example | Name | [M + H]+ m/z | $t_{R\ [min.]}$ LC-MS method |
|---|---|---|---|
| 14 | 2-(7-((5-fluorobenzo[d]oxazol-2-yl)(methyl)amino)-2-methyl-6,7,8,9-tetrahydropyrido[1,2-a]indol-10-yl)acetic acid | 408.09 | 0.91 LC-1 |
| 15 | 2-(2-chloro-7-((5-fluoropyrimidin-2-yl)(methyl)amino)-6,7,8,9-tetrahydropyrido[1,2-a]indol-10-yl)acetic acid | 388.79 | 0.93 LC-1 |
| 16 | 2-(2-chloro-7-((5-fluorobenzo[d]oxazol-2-yl)(methyl)amino)-6,7,8,9-tetrahydropyrido[1,2-a]indol-10-yl)acetic acid | 428.06 | 0.92 LC-1 |
| 17 | 2-(7-((5-chloropyrimidin-2-yl)(methyl)amino)-3-fluoro-6,7,8,9-tetrahydropyrido[1,2-a]indol-10-yl)acetic acid | 388.9 | 0.94 LC-1 |
| 18 | 2-(3-fluoro-7-(methyl(5-(trifluoromethyl)pyrimidin-2-yl)amino)-6,7,8,9-tetrahydropyrido[1,2-a]indol-10-yl)acetic acid | 422.89 | 0.96 LC-1 |
| 19 | 2-(3-fluoro-7-((5-fluorobenzo[d]thiazol-2-yl)(methyl)amino)-6,7,8,9-tetrahydropyrido[1,2-a]indol-10-yl)acetic acid | 427.75 | 0.93 LC-1 |
| 20 | 2-(3-fluoro-7-((6-fluorobenzo[d]oxazol-2-yl)(methyl)amino)-6,7,8,9-tetrahydropyrido[1,2-a]indol-10-yl)acetic acid | 411.93 | 0.87 LC-1 |
| 21 | 2-(3-chloro-7-((5-chloropyrimidin-2-yl)(methyl)amino)-6,7,8,9-tetrahydropyrido[1,2-a]indol-10-yl)acetic acid | 404.93 | 0.95 LC-2 |
| 22 | 2-(7-((5-chloropyrimidin-2-yl)(methyl)amino)-3-(trifluoromethyl)-6,7,8,9-tetrahydropyrido[1,2-a]indol-10-yl)acetic acid | 438.79 | 0.96 LC-2 |
| 23 | 2-(7-((5-chloropyrimidin-2-yl)(methyl)amino)-2-(trifluoromethoxy)-6,7,8,9-tetrahydropyrido[1,2-a]indol-10-yl)acetic acid | 454.87 | 0.98 LC-2 |
| 24 | 2-(7-((5-fluoropyrimidin-2-yl)(methyl)amino)-3-(trifluoromethyl)-6,7,8,9-tetrahydropyrido[1,2-a]indol-10-yl)acetic acid | 423 | 0.94 LC-2 |
| 25 | 2-(7-((5-fluoropyrimidin-2-yl)(methyl)amino)-2-(trifluoromethoxy)-6,7,8,9-tetrahydropyrido[1,2-a]indol-10-yl)acetic acid | 438.86 | 0.95 LC-2 |
| 26 | 2-(7-((6-fluorobenzo[d]thiazol-2-yl)(methyl)amino)-3-(trifluoromethyl)-6,7,8,9-tetrahydropyrido[1,2-a]indol-10-yl)acetic acid | 477.84 | 0.95 LC-2 |
| 27 | 2-(7-((6-fluorobenzo[d]thiazol-2-yl)(methyl)amino)-2-(trifluoromethoxy)-6,7,8,9-tetrahydropyrido[1,2-a]indol-10-yl)acetic acid | 493.83 | 0.96 LC-2 |
| 28 | 2-(7-((5-fluorobenzo[d]oxazol-2-yl)(methyl)amino)-3-(trifluoromethyl)-6,7,8,9-tetrahydropyrido[1,2-a]indol-10-yl)acetic acid | 461.69 | 0.94 LC-2 |
| 29 | 2-(7-((5-fluorobenzo[d]oxazol-2-yl)(methyl)amino)-2-(trifluoromethoxy)-6,7,8,9-tetrahydropyrido[1,2-a]indol-10-yl)acetic acid | 477.89 | 0.95 LC-2 |
| 30 | 2-(3-chloro-7-((5-fluoropyrimidin-2-yl)(methyl)amino)-6,7,8,9-tetrahydropyrido[1,2-a]indol-10-yl)acetic acid | 388.98 | 0.91 LC-2 |
| 31 | 2-(3-chloro-7-((5-fluorobenzo[d]oxazol-2-yl)(methyl)amino)-6,7,8,9-tetrahydropyrido[1,2-a]indol-10-yl)acetic acid | 427.9 | 0.92 LC-2 |
| 38 | 2-(3-chloro-7-(methyl(5-methylpyrimidin-2-yl)amino)-6,7,8,9-tetrahydropyrido[1,2-a]indol-10-yl)acetic acid | 385.16 | 0.82 LC-2 |
| 39 | 2-(3-chloro-7-(methyl(quinazolin-2-yl)amino)-6,7,8,9-tetrahydropyrido[1,2-a]indol-10-yl)acetic acid | 421.25 | 0.79 LC-2 |
| 40 | 2-(3-chloro-7-((6-fluoroquinazolin-2-yl)(methyl)amino)-6,7,8,9-tetrahydropyrido[1,2-a]indol-10-yl)acetic acid | 439.38 | 0.90 LC-2 |
| 41 | 2-(3-chloro-7-((7-fluoroquinazolin-2-yl)(methyl)amino)-6,7,8,9-tetrahydropyrido[1,2-a]indol-10-yl)acetic acid | 439.12 | 0.91 LC-2 |
| 42 | 2-(3-chloro-7-(methyl(2-methylquinazolin-4-yl)amino)-6,7,8,9-tetrahydropyrido[1,2-a]indol-10-yl)acetic acid | 435.19 | 0.72 LC-2 |
| 43 | 2-(3-chloro-7-((6-fluoroquinoxalin-2-yl)(methyl)amino)-6,7,8,9-tetrahydropyrido[1,2-a]indol-10-yl)acetic acid | 439.39 | 0.95 LC-2 |

B.1 Synthesis of (S)-2-(3-chloro-7-((5-fluoropyrimidin-2-yl)(methyl)amino)-6,7,8,9-tetrahydropyrido[1,2-a]indol-10-yl)acetic acid and (R)-2-(3-chloro-7-((5-fluoropyrimidin-2-yl)(methyl)amino)-6,7,8,9-tetrahydropyrido[1,2-a]indol-10-yl)acetic acid

B.1.1 Synthesis of (S)-methyl 2-(3-chloro-7-(methylamino)-6,7,8,9-tetrahydropyrido[1,2-a]indol-10-yl)acetate and (R)-methyl 2-(3-chloro-7-(methylamino)-6,7,8,9-tetrahydropyrido[1,2-a]indol-10-yl)acetate

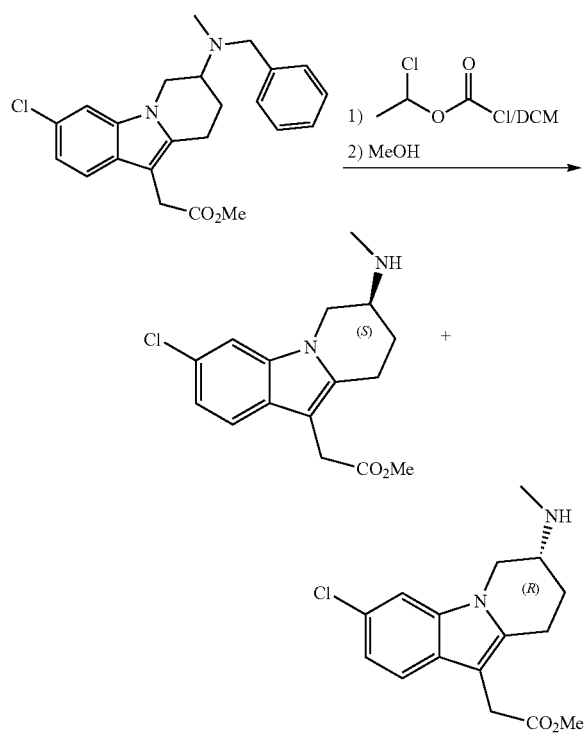

To a solution of methyl 2-(7-(benzyl(methyl)amino)-3-chloro-6,7,8,9-tetrahydropyrido[1,2-a]indol-10-yl)acetate (365 mg, 0.92 mmol) in dry DCM (13.4 ml) in a sealed tube, was added 1-chloroethyl chloroformate (0.2 ml, 1.84 mmol). The reaction mixture was stirred at 80° C. for 12 h. After cooling to rt, the reaction mixture was concentrated in vacuo. To the residue was added MeOH (13.4 ml), the reaction mixture was stirred at reflux for 1 h and concentrated in vacuo. The residue was dissolved in EA and washed with sat.NaHCO₃ solution. The aqueous phase was extracted with EA, the combined extracts were dried over MgSO₄, filtered and concentrated in vacuo. The resulting residue was purified by FC (DCM/MeOH: 10/0 to 9/1) to give the racemate as an oil.

LC-MS (LC-1): $t_R$: 0.59 min./[M+H]⁺: 306.96.

The two enantiomers of the obtained product were separated by preparative chiral HPLC (chiral HPLC-3):

(S)-methyl 2-(3-chloro-7-(methylamino)-6,7,8,9-tetrahydropyrido[1,2-a]indol-10-yl)acetate (60 mg, 21%): HPLC (chiral HPLC-1): $t_R$: 8.45 min;

(R)-methyl 2-(3-chloro-7-(methylamino)-6,7,8,9-tetrahydropyrido[1,2-a]indol-10-yl)acetate (60 mg, 21%): HPLC (chiral HPLC-1): $t_R$: 10.23 min.

B.1.2 Synthesis of (S)-2-(3-chloro-7-((5-fluoropyrimidin-2-yl)(methyl)amino)-6,7,8,9-tetrahydropyrido[1,2-a]indol-10-yl)acetic acid Example 32

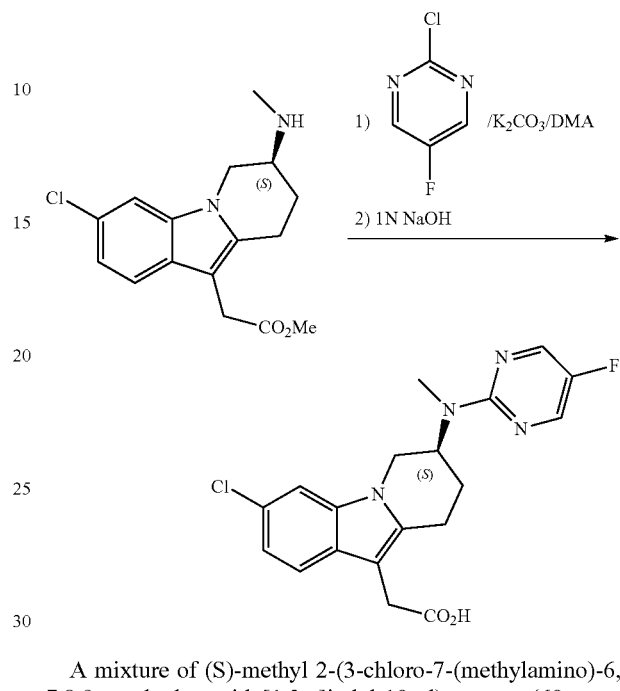

A mixture of (S)-methyl 2-(3-chloro-7-(methylamino)-6,7,8,9-tetrahydropyrido[1,2-a]indol-10-yl)acetate (60 mg, 0.19 mmol), 2-chloro-5-fluoropyrimidine (0.0175 ml, 0.19 mmol) and K₂CO₃ (65.5 mg, 0.47 mmol) in DMA (2 ml) was stirred at 130° C. for 2 days. After cooling to rt, 1N NaOH (2.5 ml) was added to the reaction mixture. The reaction mixture was stirred at rt for 2 h and then 37% HCl was added until pH 1-2. The product was directly purified by prep. HPLC to provide the title compound as an oil.

LC-MS (LC-2): $t_R$: 0.91 min./[M+H]⁺: 389.18.

HPLC (chiral HPLC-2): $t_R$: 8.6 min.

B.1.3 Synthesis of (R)-2-(3-chloro-7-((5-fluoropyrimidin-2-yl)(methyl)amino)-6,7,8,9-tetrahydropyrido[1,2-a]indol-10-yl)acetic acid Example 33

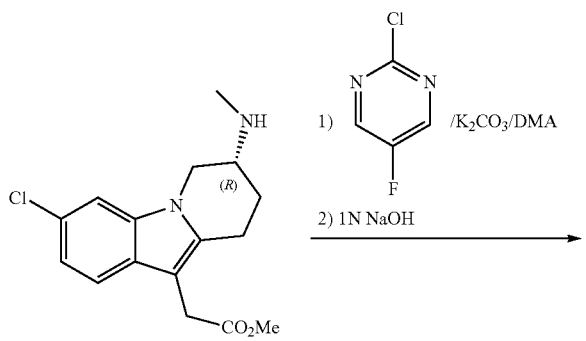

-continued

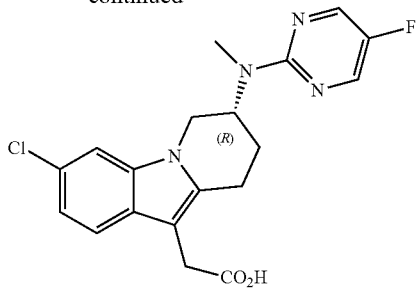

A mixture of (R)-methyl 2-(3-chloro-7-(methylamino)-6,7,8,9-tetrahydropyrido[1,2-a]indol-10-yl)acetate (60 mg, 0.19 mmol), 2-chloro-5-fluoropyrimidine (0.0175 ml, 0.19 mmol) and $K_2CO_3$ (65.5 mg, 0.47 mmol) in DMA (2 ml) was stirred at 130° C. for 2 days. After cooling to rt, 1N NaOH (2.5 ml) was added to the reaction mixture. The reaction mixture was stirred at rt for 2 h and then 37% HCl was added until pH 1-2. The product was directly purified by prep.

HPLC to provide the title compound as an oil.
LC-MS (LC-2): $t_R$: 0.91 min./[M+H]$^+$: 389.16.
HPLC (chiral HPLC-2): $t_R$: 11.25 min.

C.1 Synthesis of 2-(7-(heteroarylamino)-6,7,8,9-tetrahydropyrido[1,2-a]indol-10-yl)acetic acid derivatives ($R^3$ represents H)

C.1.1 Synthesis of tert-butyl (6,7,8,9-tetrahydropyrido[1,2-a]indol-7-yl)carbamate derivatives

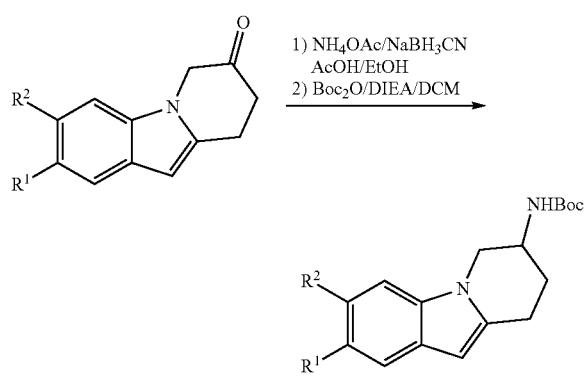

General Procedure

To a solution of the respective 8,9-dihydropyrido[1,2-a]indol-7(6H)-one derivative (0.23 mmol) in EtOH (5 ml) were added portionwise successively ammonium acetate (4.6 mmol, 20 eq) and NaBH$_3$CN (0.11 mmol, 0.5 eq). Then AcOH was added (0.3 ml) and the reaction mixture was stirred at rt for 1 h30. The reaction mixture was then quenched with water, basified until pH 9 with 1N NaOH and filtered. The filtrate was extracted twice with DCM, the combined extracts were dried over MgSO$_4$, filtered and concentrated in vacuo to give the amine which was used for the next step without further purification.

To a solution of this crude amine (0.23 mmol) in dry DCM (2 ml), were added successively Boc$_2$O (0.23 mmol) and DIEA (0.46 mmol). The reaction mixture was stirred at rt for 3 h, diluted with DCM and washed with sat. NaHCO$_3$ solution. The aqueous phase was extracted twice with DCM, the combined extracts were dried over MgSO$_4$, filtered and concentrated in vacuo. The resulting residue was purified by FC (EA/n-heptane: 0/10 to 2/8) to give the title compound as an oil.

The following tert-butyl (6,7,8,9-tetrahydropyrido[1,2-a]indol-7-yl)carbamate derivatives were synthetized according to the above general procedure.

TABLE 13

| $R^1$ | $R^2$ | Name | [M + H]$^+$ m/z | $t_R$ [min] LC-MS method |
|---|---|---|---|---|
| H | Cl | tert-butyl (3-chloro-6,7,8,9-tetrahydropyrido[1,2-a]indol-7-yl)carbamate | 321.19 | 0.98 LC-2 |
| H | F | tert-butyl (3-fluoro-6,7,8,9-tetrahydropyrido[1,2-a]indol-7-yl)carbamate | 305.08 | 1.02 LC-2 |

C.1.2 Synthesis of methyl 2-(7-amino-6,7,8,9-tetrahydropyrido[1,2-a]indol-10-yl)acetate derivatives

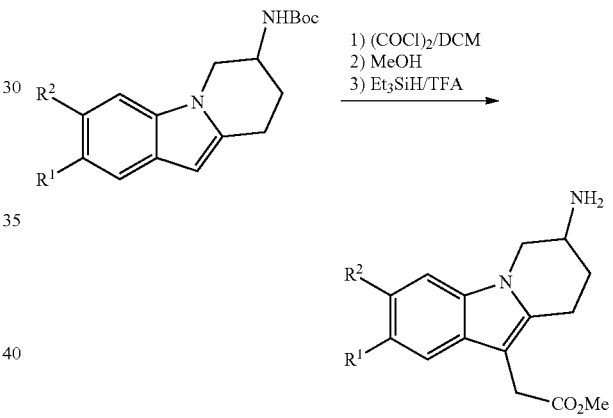

General Procedure

To a cold (0° C.) solution of the respective tert-butyl (6,7,8,9-tetrahydropyrido[1,2-a]indol-7-yl)carbamate derivative (1.4 mmol) in dry DCM (28.5 ml) was added oxalyl chloride (2.8 mmol). After stirring at 0° C. for 1 h, MeOH (2.3 ml) was added and the reaction mixture was stirred at 0° C. for 1 h, quenched with sat. NaHCO$_3$ solution. The aqueous phase was extracted with DCM, the combined extracts were dried over MgSO$_4$, filtered and concentrated in vacuo to give the keto-ester as an oil which was used for the next step without further purification.

To the crude keto-ester (1.28 mmol) in TFA (12.3 ml) was added triethylsilane (2.56 mmol). The reaction mixture was stirred at rt for 2 h and concentrated in vacuo. The resulting residue was dissolved in EA, washed with sat. NaHCO$_3$ solution, water, brine, dried over MgSO$_4$, filtered and concentrated in vacuo. The resulting residue was purified by FC (EA/n-heptane: 0/10 to 3/7) to give the title compound as a solid.

The following methyl 2-(7-amino-6,7,8,9-tetrahydropyrido[1,2-a]indol-10-yl)acetate derivatives were synthetized according to the above general procedure.

TABLE 14

| R¹ | R² | Name | [M + H]⁺ m/z | $t_R$ [min] LC-MS method |
|---|---|---|---|---|
| H | Cl | methyl 2-(7-amino-3-chloro-6,7,8,9-tetrahydropyrido[1,2-a]indol-10-yl)acetate | 293.26 | 0.64 LC-2 |
| H | F | methyl 2-(7-amino-3-fluoro-6,7,8,9-tetrahydropyrido[1,2-a]indol-10-yl)acetate | 277.08 | 0.66 LC-2 |

C.1.3 Synthesis of 2-(7-(heteroarylamino)-6,7,8,9-tetrahydropyrido[1,2-a]indol-10-yl)acetic acid derivatives

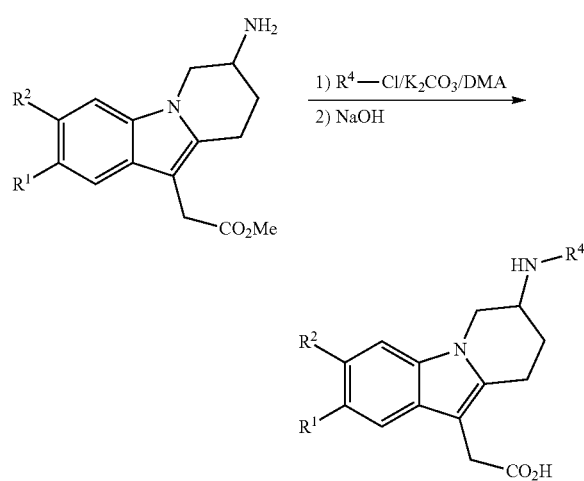

General Procedure

A mixture of the respective methyl 2-(7-amino-6,7,8,9-tetrahydropyrido[1,2-a]indol-10-yl)acetate derivative (1 mmol), the appropriate R⁴—Cl (1 mmol) and K₂CO₃ (1.5 mmol) in DMA (20 ml) was stirred at 130° C. for 12 h. After cooling to rt, 1N NaOH (20 ml) was added to the reaction mixture. The reaction mixture was stirred at rt for 2 h and then 37% HCl was added until pH 1-2. The products were directly purified by prep. HPLC to provide the final compound.

Preparation of Examples

The following 2-(7-(heteroarylamino)-6,7,8,9-tetrahydropyrido[1,2-a]indol-10-yl)acetic acid derivatives were synthetized according to the above general procedure.

TABLE 15

| Example | Name | [M + H]⁺ m/z | $t_R$ [min] LC-MS method |
|---|---|---|---|
| 34 | 2-(3-fluoro-7-((5-fluoropyrimidin-2-yl)amino)-6,7,8,9-tetrahydropyrido[1,2-a]indol-10-yl)acetic acid | 359.14 | 0.78 LC-1 |
| 35 | 2-(3-fluoro-7-((5-fluorobenzo[d]oxazol-2-yl)amino)-6,7,8,9-tetrahydropyrido[1,2-a]indol-10-yl)acetic acid | 398.03 | 0.82 LC-1 |
| 36 | 2-(3-chloro-7-((5-fluoropyrimidin-2-yl)amino)-6,7,8,9-tetrahydropyrido[1,2-a]indol-10-yl)acetic acid | 375.13 | 0.85 LC-2 |
| 37 | 2-(3-chloro-7-((5-chloropyrimidin-2-yl)amino)-6,7,8,9-tetrahydropyrido[1,2-a]indol-10-yl)acetic acid | 391.09 | 0.88 LC-2 |

D.1 Synthesis of 7-(Heteroaryl-amino)-6,7,8,9-tetrahydropyrido[1,2-a]indol acetic acid derivatives (Method B)

D.1.1 Synthesis of 7-(Heteroaryl(alkyl)amino)-6,7,8,9-tetrahydropyrido[1,2-a]indole derivatives

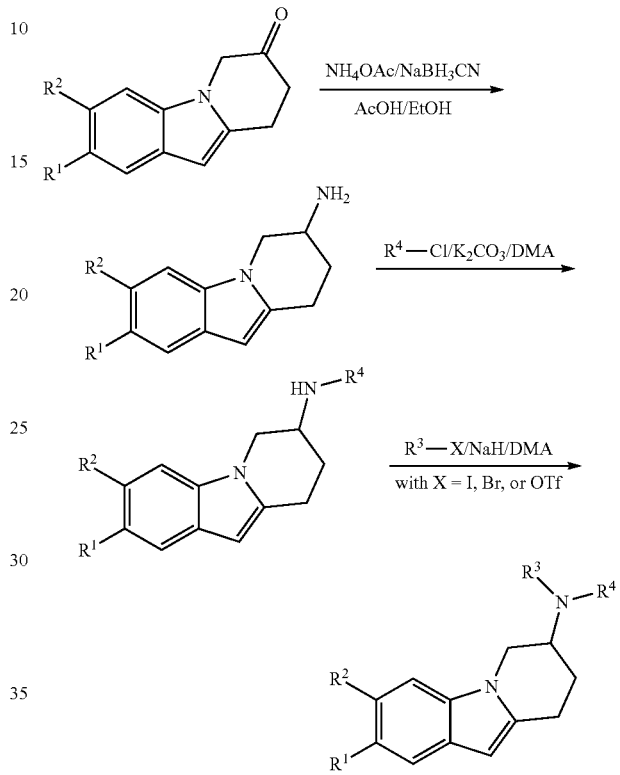

General Procedure

To a solution of the respective 8,9-dihydropyrido[1,2-a]indol-7(6H)-one derivative (9.1 mmol) in EtOH (208 ml) were added portionwise successively ammonium acetate (182 mmol, 20 eq) and NaBH₃CN (4.55 mmol, 0.5 eq). Then AcOH was added (12 ml) and the reaction mixture was stirred at rt for 1 h30. The reaction mixture was then quenched with water, basified until pH 9 with 1N NaOH and filtered. The filtrate was extracted twice with DCM, the combined extracts were dried over MgSO₄, filtered and concentrated in vacuo to give the amine which was used for the next step without further purification.

To a solution of the crude amine (0.77 mmol) in DMA (2 ml) were added successively the appropriate R⁴—Cl (0.77 mmol, 1 eq) and K₂CO₃ (1.15 mmol, 1.5 eq). The reaction mixture was stirred at 100° C. for 3 h. After cooling to rt, the mixture was diluted with EA, washed with sat. NaHCO₃ solution, water, brine, dried over MgSO₄, filtered and concentrated in vacuo. The resulting residue was purified by FC (n-heptane to n-heptane/EA: 8/2) to give the desired 7-(Heteroaryl-amino)-6,7,8,9-tetrahydropyrido[1,2-a]indole derivatives as a solid.

To a solution of the respective 7-(Heteroaryl-amino)-6,7,8,9-tetrahydropyrido[1,2-a]indole derivative (0.045 mmol) in DMA (1 ml), was added NaH (50% in mineral oil) (0.09 mmol, 2 eq).

The reaction mixture was stirred at rt for 5 min., then the appropriate R³—X (with X═I, Br or OTf) (0.45 mmol, 10 eq) was added and the reaction mixture was stirred at 50° C. for 16 h. More NaH (4 eq) and R³—X (10 eq) were added and the stirring at 50° C. was continued for 1 day. The product was directly purified by prep. HPLC to provide the title compound as an oil.

The following 7-(Heteroaryl(alkyl)amino)-6,7,8,9-tetrahydropyrido[1,2-a]indole derivatives were synthetized according to the above general procedure.

TABLE 16

| R¹ | R² | R³ | R⁴ | Name | [M + H]⁺ m/z | t_R [min] LC-MS method |
|---|---|---|---|---|---|---|
| H | Cl | 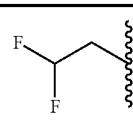 (X = OTf) | 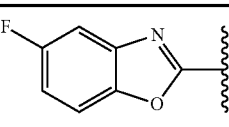 | N-(3-chloro-6,7,8,9-tetrahydropyrido[1,2-a]indol-7-yl)-N-(2,2-difluoroethyl)-5-fluorobenzo[d]oxazol-2-amine | 419.97 | 0.93 LC-2 |
| H | Cl | Et (X = I) | 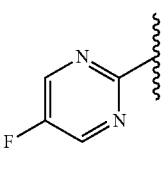 [SMILES: *c1ncc(F)cn1] | 3-chloro-N-ethyl-N-(5-fluoropyrimidin-2-yl)-6,7,8,9-tetrahydropyrido[1,2-a]indol-7-amine | 345.25 | 1.06 LC-2 |
| H | Cl | iPr (X = I) | 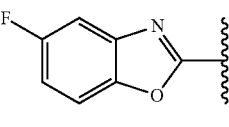 | N-(3-chloro-6,7,8,9-tetrahydropyrido[1,2-a]indol-7-yl)-5-fluoro-N-isopropylbenzo[d]oxazol-2-amine | 398.05 | 1.07 LC-2 |
| H | Cl | 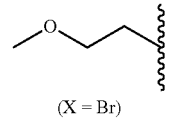 (X = Br) | 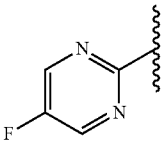 | 3-chloro-N-(5-fluoropyrimidin-2-yl)-N-(2-methoxyethyl)-6,7,8,9-tetrahydropyrido[1,2-a]indol-7-amine | 375.22 | 1.04 LC-2 |
| H | Cl | 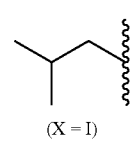 [SMILES: *CC(C)C] (X = I) | 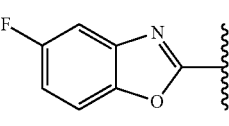 [SMILES: *c1nc2cc(F)ccc2o1] | N-(3-chloro-6,7,8,9-tetrahydropyrido[1,2-a]indol-7-yl)-5-fluoro-N-isobutylbenzo[d]oxazol-2-amine | 412.05 | 1.09 LC-2 |
| H | Cl | n-Pr (X = I) | 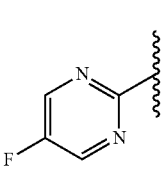 | 3-chloro-N-(5-fluoropyrimidin-2-yl)-N-propyl-6,7,8,9-tetrahydropyrido[1,2-a]indol-7-amine | 359.23 | 1.09 LC-2 |
| H | Cl | Et (X = I) | 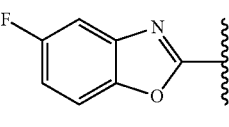 [SMILES: *c1nc2cc(F)ccc2o1] | N-(3-chloro-6,7,8,9-tetrahydropyrido[1,2-a]indol-7-yl)-N-ethyl-5-fluorobenzo[d]oxazol-2-amine | 384.03 | 1.04 LC-2 |
| H | Cl | 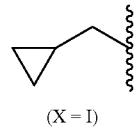 [SMILES: *CC1CC1] (X = I) | 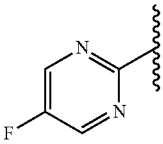 | 3-chloro-N-(cyclopropylmethyl)-N-(5-fluoropyrimidin-2-yl)-6,7,8,9-tetrahydropyrido[1,2-a]indol-7-amine | 371.22 | 1.09 LC-2 |

D.1.2 Synthesis of 7-(Heteroaryl(alkyl)amino)-6,7,8,9-tetrahydropyrido[1,2-a]indol acetic acid derivatives

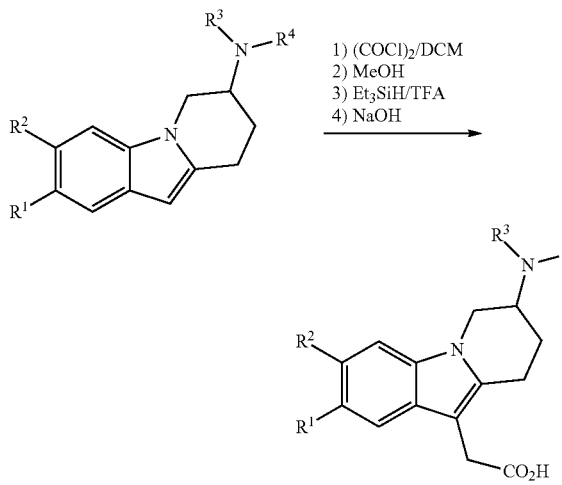

1) (COCl)$_2$/DCM
2) MeOH
3) Et$_3$SiH/TFA
4) NaOH

General Procedure

To a cold (0° C.) solution of the respective 7-(Heteroaryl(alkyl)amino)-6,7,8,9-tetrahydropyrido[1,2-a]indole derivative (0.05 mmol) in DCM (1 ml), was added oxalyl chloride (0.1 mmol, 2 eq). After stirring at 0° C. for 1 h, MeOH (0.08 ml) was added and the reaction mixture was stirred at 0° C. for 1 h, quenched with sat. NaHCO$_3$ solution. The aqueous phase was extracted with DCM, the combined extracts were dried over MgSO$_4$, filtered and concentrated in vacuo to give the keto-ester as an oil which was used for the next step without further purification.

To the crude keto-ester (0.01 mmol) in TFA (0.1 ml) was added triethylsilane (0.025 mmol, 2.5 eq). The reaction mixture was stirred at rt for 16 h and concentrated in vacuo. The resulting residue was dissolved in EA, washed with sat. NaHCO$_3$ solution, water, brine, dried over MgSO$_4$, filtered and concentrated in vacuo to provide the methyl 7-(Heteroaryl(alkyl)amino)-6,7,8,9-tetrahydropyrido[1,2-a]indol acetate derivative as an oil which was used for the next step without further purification.

To a solution of the crude methyl 7-(Heteroaryl(alkyl)amino)-6,7,8,9-tetrahydropyrido[1,2-a]indol acetate derivative (0.01 mmol) in a mixture MeCN (0.5 ml)/DMF (0.1 ml) was added 1N NaOH (1 ml). The reaction mixture was stirred at rt for 3 h, acidified with 37% HCl (0.02 ml) and purified by prep-HPLC to provide the final compound as a solid.

The following 7-(Heteroaryl(alkyl)amino)-6,7,8,9-tetrahydropyrido[1,2-a]indol acetic acid derivatives were synthetized according to the above general procedure.

TABLE 17

| Example | Name | [M + H]$^+$ m/z | $t_{R\,[min.]}$ LC-MS method |
|---|---|---|---|
| 44 | 2-(3-chloro-7-((2,2-difluoroethyl)(5-fluorobenzo[d]oxazol-2-yl)amino)-6,7,8,9-tetrahydropyrido[1,2-a]indol-10-yl)acetic acid | 478 | 0.95 LC-2 |
| 45 | 2-(3-chloro-7-(ethyl(5-fluoropyrimidin-2-yl)amino)-6,7,8,9-tetrahydropyrido[1,2-a]indol-10-yl)acetic acid | 403.13 | 0.94 LC-2 |
| 46 | 2-(3-chloro-7-((5-fluorobenzo[d]oxazol-2-yl)(isopropyl)amino)-6,7,8,9-tetrahydropyrido[1,2-a]indol-10-yl)acetic acid | 456.19 | 0.97 LC-2 |
| 47 | 2-(3-chloro-7-((5-fluoropyrimidin-2-yl)(2-methoxyethyl)amino)-6,7,8,9-tetrahydropyrido[1,2-a]indol-10-yl)acetic acid | 433.05 | 0.93 LC-2 |
| 48 | 2-(3-chloro-7-((5-fluorobenzo[d]oxazol-2-yl)(isobutyl)amino)-6,7,8,9-tetrahydropyrido[1,2-a]indol-10-yl)acetic acid | 470.2 | 1.00 LC-2 |
| 49 | 2-(3-chloro-7-((5-fluoropyrimidin-2-yl)(propyl)amino)-6,7,8,9-tetrahydropyrido[1,2-a]indol-10-yl)acetic acid | 417 | 0.98 LC-2 |
| 50 | 2-(3-chloro-7-(ethyl(5-fluorobenzo[d]oxazol-2-yl)amino)-6,7,8,9-tetrahydropyrido[1,2-a]indol-10-yl)acetic acid | 442.16 | 0.94 LC-2 |
| 51 | 2-(3-chloro-7-((cyclopropylmethyl)(5-fluoropyrimidin-2-yl)amino)-6,7,8,9-tetrahydropyrido[1,2-a]indol-10-yl)acetic acid | 429.26 | 0.99 LC-2 |

Biological Assays

Preparation of hCRTH2 Receptor Membranes and Radioligand Displacement Assay

First, recombinant HEK293-hCRTH$_2$ cells were detached from culture plates into 5 ml buffer A/plate (Buffer A: 5 mM Tris, 1 mM MgCl$_2$-6H$_2$O pH=7.4) using a rubber policeman. Cells were then transferred into centrifugation tubes and centrifuged for 5 min at 400 g. The cell pellet was resuspended in the same buffer and tubes were frozen at −80° C. Cells were thawed and membrane fragments were generated by homogenization using a polytron homogenizer (30 seconds). The membrane fragments were then centrifuged at 3000 g for 20 minutes and resuspended in buffer C (Buffer C: 75 mM Tris, 25 mM MgCl$_2$, 250 mM Saccharose pH 7.4). Aliquots of membrane fragments were stored at −20° C.

Binding assay was performed in a final assay volume of 250 μl. First, 25 μl of test compound, previously diluted in Binding-Buffer (Binding-Buffer: 50 mM Tris-Base, 100 mM NaCl, 1 mM EDTA, 0.1% BSA (protease free), 0.01% NaN$_3$, 10 mM MnCl$_2$ pH 7.0) was placed into each well. After addition of 75 μl Binding-Buffer, 50 μl of the radioligand $^3$H-PGD$_2$ (at 2.5 nM (220.000 dpm/well) from ANAWA ART0662) was added to each well. Binding assay was started by addition of 100 μl CRTH$_2$ membrane fragments, reaching a final concentration of 20 μg/well. For non-specific binding, PGD$_2$ was added to the reaction mixture to 10 mM final concentration. This assay mix was incubated for 90 minutes at room temperature and then filtered through a GF/C filter 96-well plate which was pre-soaked for 3 hours in 0.5% polyethyleneimine (PEI). The filter-wells were washed three times with ice cold Binding-Buffer. Then, 40 μl of Microscint-40 (Packard) was added to each well and the retained radioactivity quantified in a Topcount (Packard).

Antagonistic activities of exemplified compounds are displayed in Table 16.

| Example | Name | IC$_{50}$ [nM] |
|---|---|---|
| 1 | 2-(7-((5-chloropyrimidin-2-yl)(methyl)amino)-6,7,8,9-tetrahydropyrido[1,2-a]indol-10-yl)acetic acid | 21 |
| 2 | 2-(7-((5-fluoropyrimidin-2-yl)(methyl)amino)-6,7,8,9-tetrahydropyrido[1,2-a]indol-10-yl)acetic acid | 9 |
| 3 | 2-(7-(methyl(5-(trifluoromethyl)pyrimidin-2-yl)amino)-6,7,8,9-tetrahydropyrido[1,2-a]indol-10-yl)acetic acid | 8 |
| 4 | 2-(7-((6-fluorobenzo[d]thiazol-2-yl)(methyl)amino)-6,7,8,9-tetrahydropyrido[1,2-a]indol-10-yl)acetic acid | 9 |
| 5 | 2-(7-((5-fluorobenzo[d]oxazol-2-yl)(methyl)amino)-6,7,8,9-tetrahydropyrido[1,2-a]indol-10-yl)acetic acid | 16 |
| 6 | 2-(7-((5-fluorobenzo[d]thiazol-2-yl)(methyl)amino)-6,7,8,9-tetrahydropyrido[1,2-a]indol-10-yl)acetic acid | 92 |
| 7 | 2-(2-fluoro-7-((5-fluoropyrimidin-2-yl)(methyl)amino)-6,7,8,9-tetrahydropyrido[1,2-a]indol-10-yl)acetic acid | 17 |
| 8 | 2-(2-fluoro-7-((5-fluorobenzo[d]oxazol-2-yl)(methyl)amino)-6,7,8,9-tetrahydropyrido[1,2-a]indol-10-yl)acetic acid | 12 |
| 9 | 2-(3-fluoro-7-((5-fluoropyrimidin-2-yl)(methyl)amino)-6,7,8,9-tetrahydropyrido[1,2-a]indol-10-yl)acetic acid | 1 |
| 10 | 2-(3-fluoro-7-((5-fluorobenzo[d]oxazol-2-yl)(methyl)amino)-6,7,8,9-tetrahydropyrido[1,2-a]indol-10-yl)acetic acid | 0.7 |
| 11 | 2-(7-((5-fluoropyrimidin-2-yl)(methyl)amino)-2-methoxy-6,7,8,9-tetrahydropyrido[1,2-a]indol-10-yl)acetic acid | 420 |
| 12 | 2-(7-((5-fluorobenzo[d]oxazol-2-yl)(methyl)amino)-2-methoxy-6,7,8,9-tetrahydropyrido[1,2-a]indol-10-yl)acetic acid | 231 |
| 13 | 2-(7-((5-fluoropyrimidin-2-yl)(methyl)amino)-2-methyl-6,7,8,9-tetrahydropyrido[1,2-a]indol-10-yl)acetic acid | 417 |
| 14 | 2-(7-((5-fluorobenzo[d]oxazol-2-yl)(methyl)amino)-2-methyl-6,7,8,9-tetrahydropyrido[1,2-a]indol-10-yl)acetic acid | 42 |
| 15 | 2-(2-chloro-7-((5-fluoropyrimidin-2-yl)(methyl)amino)-6,7,8,9-tetrahydropyrido[1,2-a]indol-10-yl)acetic acid | 136 |
| 16 | 2-(2-chloro-7-((5-fluorobenzo[d]oxazol-2-yl)(methyl)amino)-6,7,8,9-tetrahydropyrido[1,2-a]indol-10-yl)acetic acid | 21 |
| 17 | 2-(7-((5-chloropyrimidin-2-yl)(methyl)amino)-3-fluoro-6,7,8,9-tetrahydropyrido[1,2-a]indol-10-yl)acetic acid | 4 |
| 18 | 2-(3-fluoro-7-(methyl(5-(trifluoromethyl)pyrimidin-2-yl)amino)-6,7,8,9-tetrahydropyrido[1,2-a]indol-10-yl)acetic acid | 6 |
| 19 | 2-(3-fluoro-7-((5-fluorobenzo[d]thiazol-2-yl)(methyl)amino)-6,7,8,9-tetrahydropyrido[1,2-a]indol-10-yl)acetic acid | 51 |
| 20 | 2-(3-fluoro-7-((6-fluorobenzo[d]oxazol-2-yl)(methyl)amino)-6,7,8,9-tetrahydropyrido[1,2-a]indol-10-yl)acetic acid | 1 |
| 21 | 2-(3-chloro-7-((5-chloropyrimidin-2-yl)(methyl)amino)-6,7,8,9-tetrahydropyrido[1,2-a]indol-10-yl)acetic acid | 7 |
| 22 | 2-(7-((5-chloropyrimidin-2-yl)(methyl)amino)-3-(trifluoromethyl)-6,7,8,9-tetrahydropyrido[1,2-a]indol-10-yl)acetic acid | 9 |
| 23 | 2-(7-((5-chloropyrimidin-2-yl)(methyl)amino)-2-(trifluoromethoxy)-6,7,8,9-tetrahydropyrido[1,2-a]indol-10-yl)acetic acid | 354 |
| 24 | 2-(7-((5-fluoropyrimidin-2-yl)(methyl)amino)-3-(trifluoromethyl)-6,7,8,9-tetrahydropyrido[1,2-a]indol-10-yl)acetic acid | 5 |
| 25 | 2-(7-((5-fluoropyrimidin-2-yl)(methyl)amino)-2-(trifluoromethoxy)-6,7,8,9-tetrahydropyrido[1,2-a]indol-10-yl)acetic acid | 141 |
| 26 | 2-(7-((6-fluorobenzo[d]thiazol-2-yl)(methyl)amino)-3-(trifluoromethyl)-6,7,8,9-tetrahydropyrido[1,2-a]indol-10-yl)acetic acid | 16 |

| Example | Name | IC$_{50}$ [nM] |
|---|---|---|
| 27 | 2-(7-((6-fluorobenzo[d]thiazol-2-yl)(methyl)amino)-2-(trifluoromethoxy)-6,7,8,9-tetrahydropyrido[1,2-a]indol-10-yl)acetic acid | 812 |
| 28 | 2-(7-((5-fluorobenzo[d]oxazol-2-yl)(methyl)amino)-3-(trifluoromethyl)-6,7,8,9-tetrahydropyrido[1,2-a]indol-10-yl)acetic acid | 8 |
| 29 | 2-(7-((5-fluorobenzo[d]oxazol-2-yl)(methyl)amino)-2-(trifluoromethoxy)-6,7,8,9-tetrahydropyrido[1,2-a]indol-10-yl)acetic acid | 964 |
| 30 | 2-(3-chloro-7-((5-fluoropyrimidin-2-yl)(methyl)amino)-6,7,8,9-tetrahydropyrido[1,2-a]indol-10-yl)acetic acid | 10 |
| 31 | 2-(3-chloro-7-((5-fluorobenzo[d]oxazol-2-yl)(methyl)amino)-6,7,8,9-tetrahydropyrido[1,2-a]indol-10-yl)acetic acid | 5 |
| 32 | (S)-2-(3-chloro-7-((5-fluoropyrimidin-2-yl)(methyl)amino)-6,7,8,9-tetrahydropyrido[1,2-a]indol-10-yl)acetic acid | 0.8 |
| 33 | (R)-2-(3-chloro-7-((5-fluoropyrimidin-2-yl)(methyl)amino)-6,7,8,9-tetrahydropyrido[1,2-a]indol-10-yl)acetic acid | 2 |
| 34 | 2-(3-fluoro-7-((5-fluoropyrimidin-2-yl)amino)-6,7,8,9-tetrahydropyrido[1,2-a]indol-10-yl)acetic acid | 9 |
| 35 | 2-(3-fluoro-7-((5-fluorobenzo[d]oxazol-2-yl)amino)-6,7,8,9-tetrahydropyrido[1,2-a]indol-10-yl)acetic acid | 11 |
| 36 | 2-(3-chloro-7-((5-fluoropyrimidin-2-yl)amino)-6,7,8,9-tetrahydropyrido[1,2-a]indol-10-yl)acetic acid | 65 |
| 37 | 2-(3-chloro-7-((5-chloropyrimidin-2-yl)amino)-6,7,8,9-tetrahydropyrido[1,2-a]indol-10-yl)acetic acid | 27 |
| 38 | 2-(3-chloro-7-(methyl(5-methylpyrimidin-2-yl)amino)-6,7,8,9-tetrahydropyrido[1,2-a]indol-10-yl)acetic acid | 2 |
| 39 | 2-(3-chloro-7-(methyl(quinazolin-2-yl)amino)-6,7,8,9-tetrahydropyrido[1,2-a]indol-10-yl)acetic acid | 3 |
| 40 | 2-(3-chloro-7-((6-fluoroquinazolin-2-yl)(methyl)amino)-6,7,8,9-tetrahydropyrido[1,2-a]indol-10-yl)acetic acid | 5 |
| 41 | 2-(3-chloro-7-((7-fluoroquinazolin-2-yl)(methyl)amino)-6,7,8,9-tetrahydropyrido[1,2-a]indol-10-yl)acetic acid | 1 |
| 42 | 2-(3-chloro-7-(methyl(2-methylquinazolin-4-yl)amino)-6,7,8,9-tetrahydropyrido[1,2-a]indol-10-yl)acetic acid | 71 |
| 43 | 2-(3-chloro-7-((6-fluoroquinoxalin-2-yl)(methyl)amino)-6,7,8,9-tetrahydropyrido[1,2-a]indol-10-yl)acetic acid | 2 |
| 44 | 2-(3-chloro-7-((2,2-difluoroethyl)(5-fluorobenzo[d]oxazol-2-yl)amino)-6,7,8,9-tetrahydropyrido[1,2-a]indol-10-yl)acetic acid | 3 |
| 45 | 2-(3-chloro-7-(ethyl(5-fluoropyrimidin-2-yl)amino)-6,7,8,9-tetrahydropyrido[1,2-a]indol-10-yl)acetic acid | 1 |
| 46 | 2-(3-chloro-7-((5-fluorobenzo[d]oxazol-2-yl)(isopropyl)amino)-6,7,8,9-tetrahydropyrido[1,2-a]indol-10-yl)acetic acid | 3 |
| 47 | 2-(3-chloro-7-((5-fluoropyrimidin-2-yl)(2-methoxyethyl)amino)-6,7,8,9-tetrahydropyrido[1,2-a]indol-10-yl)acetic acid | 0.8 |
| 48 | 2-(3-chloro-7-((5-fluorobenzo[d]oxazol-2-yl)(isobutyl)amino)-6,7,8,9-tetrahydropyrido[1,2-a]indol-10-yl)acetic acid | 2 |
| 49 | 2-(3-chloro-7-((5-fluoropyrimidin-2-yl)(propyl)amino)-6,7,8,9-tetrahydropyrido[1,2-a]indol-10-yl)acetic acid | 1 |
| 50 | 2-(3-chloro-7-(ethyl(5-fluorobenzo[d]oxazol-2-yl)amino)-6,7,8,9-tetrahydropyrido[1,2-a]indol-10-yl)acetic acid | 1 |
| 51 | 2-(3-chloro-7-((cyclopropylmethyl)(5-fluoropyrimidin-2-yl)amino)-6,7,8,9-tetrahydropyrido[1,2-a]indol-10-yl)acetic acid | 0.6 |

Radioligand Displacement Assay-Human Serum Albumin (HSA)

Radioligand displacement assay in presence of human serum albumin (HSA) was performed as described above, with following modifications. Binding-Buffer-HSA: Binding-buffer+0.5% Sigma Albumin from Human serum A1887 (instead of 0.1% BSA). A volume of 25 µl test compound, previously diluted in Binding-Buffer-HSA was placed into each well. After addition of 75 µl Binding-Buffer-HSA, 50 µl of $^3$H-PGD$_2$ (at 2.5 nM (220.000 dpm/well) from ANAWA ART0662) was added to each well. Remaining protocol was identical as described above.

Antagonistic activities of exemplified compounds are displayed in Table 17.

| Example | Name | IC$_{50}$ [nM] |
|---|---|---|
| 1 | 2-(7-((5-chloropyrimidin-2-yl)(methyl)amino)-6,7,8,9-tetrahydropyrido[1,2-a]indol-10-yl)acetic acid | 66 |
| 2 | 2-(7-((5-fluoropyrimidin-2-yl)(methyl)amino)-6,7,8,9-tetrahydropyrido[1,2-a]indol-10-yl)acetic acid | 29 |
| 3 | 2-(7-(methyl(5-(trifluoromethyl)pyrimidin-2-yl)amino)-6,7,8,9-tetrahydropyrido[1,2-a]indol-10-yl)acetic acid | 152 |

-continued

| Example | Name | IC$_{50}$ [nM] |
|---|---|---|
| 4 | 2-(7-((6-fluorobenzo[d]thiazol-2-yl)(methyl)amino)-6,7,8,9-tetrahydropyrido[1,2-a]indol-10-yl)acetic acid | 43 |
| 5 | 2-(7-((5-fluorobenzo[d]oxazol-2-yl)(methyl)amino)-6,7,8,9-tetrahydropyrido[1,2-a]indol-10-yl)acetic acid | 24 |
| 6 | 2-(7-((5-fluorobenzo[d]thiazol-2-yl)(methyl)amino)-6,7,8,9-tetrahydropyrido[1,2-a]indol-10-yl)acetic acid | 59 |
| 7 | 2-(2-fluoro-7-((5-fluoropyrimidin-2-yl)(methyl)amino)-6,7,8,9-tetrahydropyrido[1,2-a]indol-10-yl)acetic acid | 119 |
| 8 | 2-(2-fluoro-7-((5-fluorobenzo[d]oxazol-2-yl)(methyl)amino)-6,7,8,9-tetrahydropyrido[1,2-a]indol-10-yl)acetic acid | 123 |
| 9 | 2-(3-fluoro-7-((5-fluoropyrimidin-2-yl)(methyl)amino)-6,7,8,9-tetrahydropyrido[1,2-a]indol-10-yl)acetic acid | 10 |
| 10 | 2-(3-fluoro-7-((5-fluorobenzo[d]oxazol-2-yl)(methyl)amino)-6,7,8,9-tetrahydropyrido[1,2-a]indol-10-yl)acetic acid | 7 |
| 14 | 2-(7-((5-fluorobenzo[d]oxazol-2-yl)(methyl)amino)-2-methyl-6,7,8,9-tetrahydropyrido[1,2-a]indol-10-yl)acetic acid | >1000 |
| 16 | 2-(2-chloro-7-((5-fluorobenzo[d]oxazol-2-yl)(methyl)amino)-6,7,8,9-tetrahydropyrido[1,2-a]indol-10-yl)acetic acid | >1000 |
| 17 | 2-(7-((5-chloropyrimidin-2-yl)(methyl)amino)-3-fluoro-6,7,8,9-tetrahydropyrido[1,2-a]indol-10-yl)acetic acid | 46 |
| 18 | 2-(3-fluoro-7-(methyl(5-(trifluoromethyl)pyrimidin-2-yl)amino)-6,7,8,9-tetrahydropyrido[1,2-a]indol-10-yl)acetic acid | 71 |
| 20 | 2-(3-fluoro-7-((6-fluorobenzo[d]oxazol-2-yl)(methyl)amino)-6,7,8,9-tetrahydropyrido[1,2-a]indol-10-yl)acetic acid | 20 |
| 21 | 2-(3-chloro-7-((5-chloropyrimidin-2-yl)(methyl)amino)-6,7,8,9-tetrahydropyrido[1,2-a]indol-10-yl)acetic acid | 31 |
| 22 | 2-(7-((5-chloropyrimidin-2-yl)(methyl)amino)-3-(trifluoromethyl)-6,7,8,9-tetrahydropyrido[1,2-a]indol-10-yl)acetic acid | 38 |
| 24 | 2-(7-((5-fluoropyrimidin-2-yl)(methyl)amino)-3-(trifluoromethyl)-6,7,8,9-tetrahydropyrido[1,2-a]indol-10-yl)acetic acid | 11 |
| 26 | 2-(7-((6-fluorobenzo[d]thiazol-2-yl)(methyl)amino)-3-(trifluoromethyl)-6,7,8,9-tetrahydropyrido[1,2-a]indol-10-yl)acetic acid | 15 |
| 28 | 2-(7-((5-fluorobenzo[d]oxazol-2-yl)(methyl)amino)-3-(trifluoromethyl)-6,7,8,9-tetrahydropyrido[1,2-a]indol-10-yl)acetic acid | 20 |
| 30 | 2-(3-chloro-7-((5-fluoropyrimidin-2-yl)(methyl)amino)-6,7,8,9-tetrahydropyrido[1,2-a]indol-10-yl)acetic acid | 9 |
| 31 | 2-(3-chloro-7-((5-fluorobenzo[d]oxazol-2-yl)(methyl)amino)-6,7,8,9-tetrahydropyrido[1,2-a]indol-10-yl)acetic acid | 13 |
| 32 | (S)-2-(3-chloro-7-((5-fluoropyrimidin-2-yl)(methyl)amino)-6,7,8,9-tetrahydropyrido[1,2-a]indol-10-yl)acetic acid | 2 |
| 33 | (R)-2-(3-chloro-7-((5-fluoropyrimidin-2-yl)(methyl)amino)-6,7,8,9-tetrahydropyrido[1,2-a]indol-10-yl)acetic acid | 57 |
| 34 | 2-(3-fluoro-7-((5-fluoropyrimidin-2-yl)amino)-6,7,8,9-tetrahydropyrido[1,2-a]indol-10-yl)acetic acid | 304 |
| 35 | 2-(3-fluoro-7-((5-fluorobenzo[d]oxazol-2-yl)amino)-6,7,8,9-tetrahydropyrido[1,2-a]indol-10-yl)acetic acid | 20 |
| 36 | 2-(3-chloro-7-((5-fluoropyrimidin-2-yl)amino)-6,7,8,9-tetrahydropyrido[1,2-a]indol-10-yl)acetic acid | 465 |
| 37 | 2-(3-chloro-7-((5-chloropyrimidin-2-yl)amino)-6,7,8,9-tetrahydropyrido[1,2-a]indol-10-yl)acetic acid | 385 |
| 38 | 2-(3-chloro-7-(methyl(5-methylpyrimidin-2-yl)amino)-6,7,8,9-tetrahydropyrido[1,2-a]indol-10-yl)acetic acid | 246 |
| 39 | 2-(3-chloro-7-(methyl(quinazolin-2-yl)amino)-6,7,8,9-tetrahydropyrido[1,2-a]indol-10-yl)acetic acid | 5 |
| 40 | 2-(3-chloro-7-((6-fluoroquinazolin-2-yl)(methyl)amino)-6,7,8,9-tetrahydropyrido[1,2-a]indol-10-yl)acetic acid | 4 |
| 41 | 2-(3-chloro-7-((7-fluoroquinazolin-2-yl)(methyl)amino)-6,7,8,9-tetrahydropyrido[1,2-a]indol-10-yl)acetic acid | 37 |
| 43 | 2-(3-chloro-7-((6-fluoroquinoxalin-2-yl)(methyl)amino)-6,7,8,9-tetrahydropyrido[1,2-a]indol-10-yl)acetic acid | 12 |
| 44 | 2-(3-chloro-7-((2,2-difluoroethyl)(5-fluorobenzo[d]oxazol-2-yl)amino)-6,7,8,9-tetrahydropyrido[1,2-a]indol-10-yl)acetic acid | 6 |
| 45 | 2-(3-chloro-7-(ethyl(5-fluoropyrimidin-2-yl)amino)-6,7,8,9-tetrahydropyrido[1,2-a]indol-10-yl)acetic acid | 3 |
| 46 | 2-(3-chloro-7-((5-fluorobenzo[d]oxazol-2-yl)(isopropyl)amino)-6,7,8,9-tetrahydropyrido[1,2-a]indol-10-yl)acetic acid | 5 |
| 47 | 2-(3-chloro-7-((5-fluoropyrimidin-2-yl)(2-methoxyethyl)amino)-6,7,8,9-tetrahydropyrido[1,2-a]indol-10-yl)acetic acid | 69 |
| 48 | 2-(3-chloro-7-((5-fluorobenzo[d]oxazol-2-yl)(isobutyl)amino)-6,7,8,9-tetrahydropyrido[1,2-a]indol-10-yl)acetic acid | 6 |
| 49 | 2-(3-chloro-7-((5-fluoropyrimidin-2-yl)(propyl)amino)-6,7,8,9-tetrahydropyrido[1,2-a]indol-10-yl)acetic acid | 21 |
| 50 | 2-(3-chloro-7-(ethyl(5-fluorobenzo[d]oxazol-2-yl)amino)-6,7,8,9-tetrahydropyrido[1,2-a]indol-10-yl)acetic acid | 9 |

| Example | Name | IC$_{50}$ [nM] |
|---|---|---|
| 51 | 2-(3-chloro-7-((cyclopropylmethyl)(5-fluoropyrimidin-2-yl)amino)-6,7,8,9-tetrahydropyrido[1,2-a]indol-10-yl)acetic acid | 9 |

Intracellular Calcium Mobilization Assay (FLIPR)

Cells (HEK-293), stably expressing the hCRTH2 receptor under the control of the cytomegalovirus promotor from a single insertion of the expression vector pcDNA5 (Invitrogen), are grown to confluency in DMEM (low glucose, Gibco) medium supplemented with 10% fetal calf serum (Bioconcept, Switzerland) under standard mammalian cell culture conditions (37° C. in a humidified atmosphere of 5% $CO_2$). Cells are detached from culture dishes using a dissociation buffer (0.02% EDTA in PBS, Gibco) for 1 min, and collected by centrifugation at 200 g at rt for 5 min in assay buffer (equal parts of Hank's BSS (HBSS, Bioconcept) and DMEM (low glucose, without phenol red, Gibco)). After incubation for 45 min (37° C. and 5% $CO_2$) in the presence of 1 μM Fluo-4 and 0.04% Pluronic F-127 (both Molecular Probes), and 20 mM HEPES (Gibco) in assay buffer, the cells are washed with and resuspended in assay buffer, then seeded onto 384-well FLIPR assay plates (Greiner) at 50,000 cells in 66 μl per well, and sedimented by centrifugation.

Stock solutions of test compounds are made up at a concentration of 10 mM in DMSO, and serially diluted in assay buffer to concentrations required for inhibition dose response curves. Prostaglandin $D_2$ (Biomol, Plymouth Meeting, Pa.) is used as an agonist.

A FLIPR Tetra instrument (Molecular Devices) is operated according to the manufacturer's standard instructions, adding 4 μl of test compound dissolved at 10 mM in DMSO and diluted prior to the experiment in assay buffer to obtain the desired final concentration. 10 μl of 80 nM prostaglandin $D_2$ (Biomol, Plymouth Meeting, Pa.) in assay buffer, supplemented with 0.8% bovine serum albumin (fatty acid content <0.02%, Sigma), is then added to obtain a final concentration of 10 nM and 0.1%, respectively. Changes in fluorescence are monitored before and after the addition of test compounds at $\lambda_{ex}$=488 nm and $\lambda_{em}$=540 nm. Emission peak values above base level after prostaglandin $D_2$ addition are exported after base line subtraction. Values are normalized to high-level control (no test compound added) after subtraction of base line value (no prostaglandin $D_2$ added). The program XLIfit 3.0 (IDBS) is used to fit the data to a single site dose response curve of the equation $(A+((B-A)/(1+((C/x)^D))))$ and to calculate the IC$_{50}$ values.

The invention claimed is:

1. A compound of formula (I):

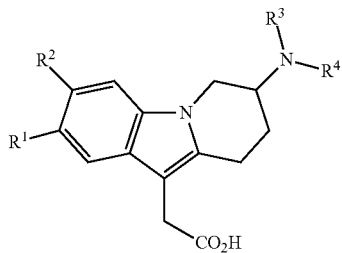

(I)

wherein $R^1$ and $R^2$ represent independently of each other hydrogen, $(C_1-C_4)$alkyl, $(C_1-C_4)$alkoxy, halogen, trifluoromethoxy or trifluoromethyl;

$R^3$ represents hydrogen, $(C_1-C_4)$alkyl, $(C_1-C_2)$alkoxy-$(C_2-C_3)$alkyl, $(C_1-C_4)$fluoroalkyl or $(C_3-C_6)$cycloalkyl-$(C_1-C_2)$alkyl; and $R^4$ represents a heteroaryl group which is unsubstituted or mono-, di- or tri-substituted, wherein the substituents are independently selected from halogen, $(C_1-C_4)$alkyl, $(C_3-C_6)$cycloalkyl, $(C_1-C_4)$alkoxy, $(C_1-C_4)$fluoroalkyl or phenyl;

or a salt thereof.

2. The compound according to claim 1, wherein $R^1$ represents hydrogen, $(C_1-C_4)$alkyl, $(C_1-C_4)$alkoxy, halogen or trifluoromethoxy;

$R^2$ represents hydrogen, halogen or trifluoromethyl;

$R^3$ represents hydrogen or $(C_1-C_4)$alkyl; and $R^4$ represents a heteroaryl group which is unsubstituted or mono- or di-substituted, wherein the substituents are independently selected from halogen or $(C_1-C_4)$fluoroalkyl;

or a salt thereof.

3. The compound according to claim 1, wherein $R^1$ represents hydrogen;

$R^2$ represents hydrogen, fluoro, chloro or trifluoromethyl;

$R^3$ represents methyl; and $R^4$ represents a heteroaryl group which is mono-substituted with fluoro or chloro, wherein the heteroaryl group is pyrimidin-2-yl, benzoxazol-2-yl or benzothiazol-2-yl;

or a salt thereof.

4. The compound according to claim 2, wherein $R^1$ represents hydrogen; or a salt thereof.

5. The compound according to claim 4, wherein $R^2$ represents hydrogen, halogen or trifluoromethyl;

or a salt thereof.

6. The compound according to claim 4, wherein $R^2$ represents fluoro or chloro;

or a salt thereof.

7. The compound according to claim 4, wherein $R^3$ represents hydrogen or methyl;

or a salt thereof.

8. The compound according to claim 4, wherein $R^4$ represents a heteroaryl group which is mono-substituted with halogen or $(C_1-C_4)$fluoroalkyl;

or a salt thereof.

9. The compound according to claim 8, wherein the heteroaryl group is pyrimidyl, benzoxazolyl or benzothiazolyl;

or a salt thereof.

10. The compound according to claim 1, wherein the compound is:

2-(7-((5-chloropyrimidin-2-yl)(methyl)amino)-6,7,8,9-tetrahydropyrido[1,2-a]indol-10-yl)acetic acid;

2-(7-((5-fluoropyrimidin-2-yl)(methyl)amino)-6,7,8,9-tetrahydropyrido[1,2-a]indol-10-yl)acetic acid;

2-(7-(methyl(5-(trifluoromethyl)pyrimidin-2-yl)amino)-6,7,8,9-tetrahydropyrido[1,2-a]indol-10-yl)acetic acid;

2-(7-((6-fluorobenzo[d]thiazol-2-yl)(methyl)amino)-6,7,8,9-tetrahydropyrido[1,2-a]indol-10-yl)acetic acid;

2-(7-((5-fluorobenzo[d]oxazol-2-yl)(methyl)amino)-6,7,8,9-tetrahydropyrido[1,2-a]indol-10-yl)acetic acid;

2-(7-((5-fluorobenzo[d]thiazol-2-yl)(methyl)amino)-6,7,8,9-tetrahydropyrido[1,2-a]indol-10-yl)acetic acid;

2-(2-fluoro-7-((5-fluoropyrimidin-2-yl)(methyl)amino)-6,7,8,9-tetrahydropyrido[1,2-a]indol-10-yl)acetic acid, 2-(2-fluoro-7-((5-fluorobenzo[d]oxazol-2-yl)(methyl)amino)-6,7,8,9-tetrahydropyrido[1,2-a]indol-10-yl)acetic acid;

2-(3-fluoro-7-((5-fluoropyrimidin-2-yl)(methyl)amino)-6,7,8,9-tetrahydropyrido[1,2-a]indol-10-yl)acetic acid;

2-(3-fluoro-7-((5-fluorobenzo[d]oxazol-2-yl)(methyl)amino)-6,7,8,9-tetrahydropyrido[1,2-a]indol-10-yl)acetic acid;

2-(7-((5-fluoropyrimidin-2-yl)(methyl)amino)-2-methoxy-6,7,8,9-tetrahydropyrido[1,2-a]indol-10-yl)acetic acid;

2-(7-((5-fluorobenzo[d]oxazol-2-yl)(methyl)amino)-2-methoxy-6,7,8,9-tetrahydropyrido[1,2-a]indol-10-yl)acetic acid;

2-(7-((5-fluoropyrimidin-2-yl)(methyl)amino)-2-methyl-6,7,8,9-tetrahydropyrido[1,2-a]indol-10-yl)acetic acid;

2-(7-((5-fluorobenzo[d]oxazol-2-yl)(methyl)amino)-2-methyl-6,7,8,9-tetrahydropyrido[1,2-a]indol-10-yl)acetic acid;

2-(2-chloro-7-((5-fluoropyrimidin-2-yl)(methyl)amino)-6,7,8,9-tetrahydropyrido[1,2-a]indol-10-yl)acetic acid;

2-(2-chloro-7-((5-fluorobenzo[d]oxazol-2-yl)(methyl)amino)-6,7,8,9-tetrahydropyrido[1,2-a]indol-10-yl)acetic acid;

2-(7-((5-chloropyrimidin-2-yl)(methyl)amino)-3-fluoro-6,7,8,9-tetrahydropyrido[1,2-a]indol-10-yl)acetic acid;

2-(3-fluoro-7-(methyl(5-(trifluoromethyl)pyrimidin-2-yl)amino)-6,7,8,9-tetrahydropyrido[1,2-a]indol-10-yl)acetic acid;

2-(3-fluoro-7-((5-fluorobenzo[d]thiazol-2-yl)(methyl)amino)-6,7,8,9-tetrahydropyrido[1,2-a]indol-10-yl)acetic acid;

2-(3-fluoro-7-((6-fluorobenzo[d]oxazol-2-yl)(methyl)amino)-6,7,8,9-tetrahydropyrido[1,2-a]indol-10-yl)acetic acid;

2-(3-chloro-7-((5-chloropyrimidin-2-yl)(methyl)amino)-6,7,8,9-tetrahydropyrido[1,2-a]indol-10-yl)acetic acid;

2-(7-((5-chloropyrimidin-2-yl)(methyl)amino)-3-(trifluoromethyl)-6,7,8,9-tetrahydropyrido[1,2-a]indol-10-yl)acetic acid;

2-(7-((5-chloropyrimidin-2-yl)(methyl)amino)-2-(trifluoromethoxy)-6,7,8,9-tetrahydropyrido[1,2-a]indol-10-yl)acetic acid;

2-(7-((5-fluoropyrimidin-2-yl)(methyl)amino)-3-(trifluoromethyl)-6,7,8,9-tetrahydropyrido[1,2-a]indol-10-yl)acetic acid;

2-(7-((5-fluoropyrimidin-2-yl)(methyl)amino)-2-(trifluoromethoxy)-6,7,8,9-tetrahydropyrido[1,2-a]indol-10-yl)acetic acid;

2-(7-((6-fluorobenzo[d]thiazol-2-yl)(methyl)amino)-3-(trifluoromethyl)-6,7,8,9-tetrahydropyrido[1,2-a]indol-10-yl)acetic acid;

2-(7-((6-fluorobenzo[d]thiazol-2-yl)(methyl)amino)-2-(trifluoromethoxy)-6,7,8,9-tetrahydropyrido[1,2-a]indol-10-yl)acetic acid;

2-(7-((5-fluorobenzo[d]oxazol-2-yl)(methyl)amino)-3-(trifluoromethyl)-6,7,8,9-tetrahydropyrido[1,2-a]indol-10-yl)acetic acid;

2-(7-((5-fluorobenzo[d]oxazol-2-yl)(methyl)amino)-2-(trifluoromethoxy)-6,7,8,9-tetrahydropyrido[1,2-a]indol-10-yl)acetic acid;

2-(3-chloro-7-((5-fluoropyrimidin-2-yl)(methyl)amino)-6,7,8,9-tetrahydropyrido[1,2-a]indol-10-yl)acetic acid;

2-(3-chloro-7-((5-fluorobenzo[d]oxazol-2-yl)(methyl)amino)-6,7,8,9-tetrahydropyrido[1,2-a]indol-10-yl)acetic acid;

(S)-2-(3-chloro-7-((5-fluoropyrimidin-2-yl)(methyl)amino)-6,7,8,9-tetrahydropyrido[1,2-a]indol-10-yl)acetic acid;

(R)-2-(3-chloro-7-((5-fluoropyrimidin-2-yl)(methyl)amino)-6,7,8,9-tetrahydropyrido[1,2-a]indol-10-yl)acetic acid;

2-(3-fluoro-7-((5-fluoropyrimidin-2-yl)amino)-6,7,8,9-tetrahydropyrido[1,2-a]indol-10-yl)acetic acid;

2-(3-fluoro-7-((5-fluorobenzo[d]oxazol-2-yl)amino)-6,7,8,9-tetrahydropyrido[1,2-a]indol-10-yl)acetic acid;

2-(3-chloro-7-((5-fluoropyrimidin-2-yl)amino)-6,7,8,9-tetrahydropyrido[1,2-a]indol-10-yl)acetic acid; or 2-(3-chloro-7-((5-chloropyrimidin-2-yl)amino)-6,7,8,9-tetrahydropyrido[1,2-a]indol-10-yl)acetic acid;

or a salt thereof.

11. A pharmaceutical composition comprising the compound according to claim 1, or a pharmaceutically acceptable salt thereof, and a pharmaceutically acceptable carrier.

12. A medicament comprising the compound according to claim 1, or a pharmaceutically acceptable salt thereof.

13. A method for treating a disease comprising administering an effective amount to a patient in need thereof the compound according to claim 1, or a pharmaceutically acceptable salt thereof, wherein the disease is asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, anaphylactic shock, urticaria, eczema, or chronic obstructive pulmonary disease (COPD).

14. A method for treating a disease comprising administering an effective amount to a patient in need thereof the compound according to claim 1, or a pharmaceutically acceptable salt thereof, wherein the disease is small vessel vasculitides, eosinophilic cellulitis (Wells syndrome).

15. A method for the treatment of a disease, comprising administering to a patient in need thereof the compound according to claim 10, or a pharmaceutically acceptable salt thereof, wherein the administered amount is effective to treat the disease, wherein the disease is asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, anaphylactic shock, urticaria, eczema or chronic obstructive pulmonary disease (COPD).

16. A method for the treatment of a disease, comprising administering to a patient in need thereof the compound according to claim 10, or a pharmaceutically acceptable salt thereof, wherein the administered amount is effective to treat the disease, wherein the disease is small vessel vasculitides, eosinophilic esophagitis or eosinophilic cellulitis (Wells syndrome).

17. The method according to claim 14, wherein the small vessel vasculitides is Churg-Strauss syndrome.

18. The method according to claim 16, wherein the small vessel vasculitides is Churg-Strauss syndrome.

* * * * *